Figure 1:
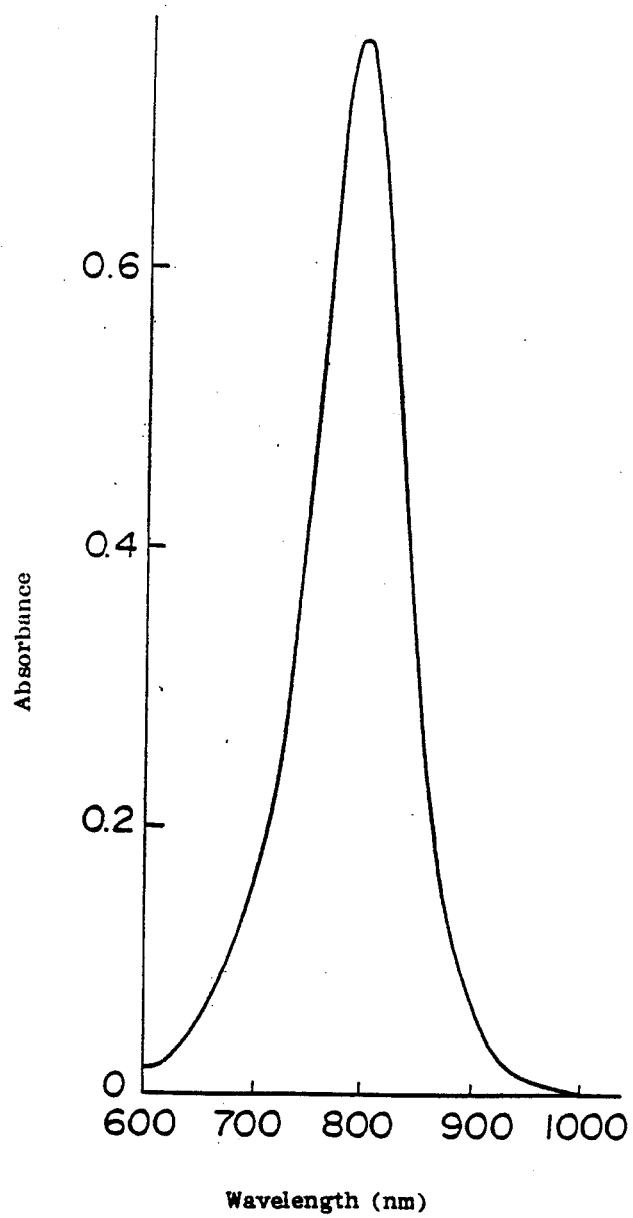

United States Patent [19]

Maeda et al.

[11] Patent Number: 4,954,420

[45] Date of Patent: Sep. 4, 1990

[54] METAL-CONTAINING INDOANILINE COMPOUND AND OPTICAL RECORDING MEDIUM EMPLOYING THE COMPOUND

[75] Inventors: Shuichi Maeda, Saitama; Toshio Kaneko, Ebina; Yutaka Kurose, Kawasaki; Michiyo Kimura, Shizuoka; Hidemi Yoshida, Atsugi; Kenichi Uchino, Tama; Shizue Inaba, Yokohama, all of Japan

[73] Assignee: Mitsubishi Kasei Corporation, Tokyo, Japan

[21] Appl. No.: 251,364

[22] Filed: Sep. 30, 1988

[30] Foreign Application Priority Data

Oct. 2, 1987 [JP] Japan .................................. 62-249519
Mar. 11, 1988 [JP] Japan .................................. 63-57846

[51] Int. Cl.$^5$ .......................... G11B 7/24; G03C 1/72
[52] U.S. Cl. .................................... 430/270; 430/495; 430/945; 546/7; 546/10
[58] Field of Search .................... 430/270, 495, 945; 546/7, 10

[56] References Cited

U.S. PATENT DOCUMENTS

| | | | |
|---|---|---|---|
| 4,547,444 | 10/1985 | Bell et al. | 430/11 |
| 4,737,443 | 4/1988 | Niwa et al. | 430/270 |
| 4,756,987 | 7/1988 | Maeda et al. | 430/270 |

FOREIGN PATENT DOCUMENTS 227569 9/1988 Japan .

OTHER PUBLICATIONS

Kubo et al., "Syntheses and Characteristics of Near-Infrared Absorbing Metal Complex Dyes with Indoaniline-Type Ligands", *Chemistry Letters*, No. 8, 1987, pp. 1563–1566.

Primary Examiner—Paul R. Michl
Assistant Examiner—Mark R. Buscher
Attorney, Agent, or Firm—Oblon, Spivak, McClelland, Maier & Neustadt

[57] ABSTRACT

A metal-containing indoaniline compound having the formula:

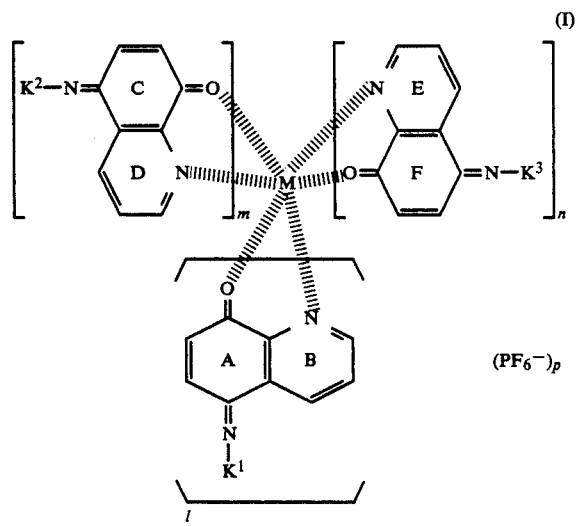

wherein M is a metal atom of Group VIII, Ib, IIb, IIIb, IVa, Va, VIa or VIIa of the Periodic Table or its halide or oxide, rings A, B, C, D, E and F may have substituents, each of $K^1$, $K^2$ and $K^3$ is a residue of a substituted or unsubstituted aromatic amine, each of l, m and n is 0 or 1, provided l+m+n=2 or 3, and p is 2, 3 or 4.

8 Claims, 2 Drawing Sheets

METAL-CONTAINING INDOANILINE COMPOUND AND OPTICAL RECORDING MEDIUM EMPLOYING THE COMPOUND

The present invention relates to a novel metal-containing indoaniline compound and an optical recording medium employing the compound.

In recent years, the optical recording utilizing laser has been developed particularly for the storage of high density information recording and reproduction of the recorded information.

An optical disc may be mentioned as a typical example of such optical recording medium.

In general, the optical disc is designed for high density information recording which is effected by irradiation of a laser beam collimated to have a diameter of about 1 μm onto a thin recording layer formed on a substrate of a disc shape. The information recording is effected by a thermal deformation of the recording layer, such as the decomposition, evaporation or dissolution, which takes place upon absorption of the laser beam energy at the irradiated portions of the recording layer. On the other hand, the reproduction of the recorded information is done by reading a difference in the reflectance between the portion thermally deformed by the laser beam and the portion where no such deformation has occurred.

Accordingly, the optical recording medium is required to have high absorptivity for a laser beam of a particular wavelength used for the recording since it is required to absorb the energy of the laser beam efficiently, and also to have a high reflectance to the laser beam of a particular wavelength for use in the reproduction so as to carry out the accurate reproduction of the recorded information.

Various constructions have been proposed for the optical recording medium of this type.

For example, Japanese Unexamined Patent Publication No. 97033/1980 discloses a medium having a single layer of a phthalocyanine dye formed on a substrate. However, the phthalocyanine dye is poor in the sensitivity and has a difficulty such that its decomposition temperature is high and its vapor deposition is difficult. Besides, its solibility in an organic solvent is extremely poor, and it is hardly possible to apply it by coating.

Japanese Unexamined Patent Publiucation No. 83344/1983 discloses a recording medium having a recording layer composed of a phenalene dye, and Japanese Unexamined Patent Publication No. 224793/1983 discloses a recording medium having a recording layer composed of a naphthoquinone dye. However, such a dye has a drawback that the reflectivity is low while it has an advantage that it can readily be vapor-deposited. If the reflectivity is low, the contrast in the reflectance between the non-recorded portion and the recorded portion irradiated with the laser beam tends to be low, and the reproduction of the recorded information tends to be difficult. Further, in general, an organic dye has a drawback that it is inferior in the storage stability.

With respect to these problems, Japanese Patent Application No. 59777/1987 proposes a medium having a metal-containing indoaniline compound incorporated in the recording layer as a medium having improved reflectance (contrast) and solubility to an organic solvent. However, such a medium has some problems as a recording medium required to have a well balanced properties with respect to both the initial characteristics (the dependency of sensitivity on the thickness of the recording layer, the secondary distorsion) and the storage stability (the coating layer, the pigment powder).

It is an object of the present invention to provide a novel metal-containing indoaniline compound having $PF_6^-$ as a counter anion which provides well balanced properties with respect to both the initial characteristics and the storage stability as a recording medium and to provide an optical recording medium employing such a compound.

The present invention provides a metal-containing indoaniline compound having the formula:

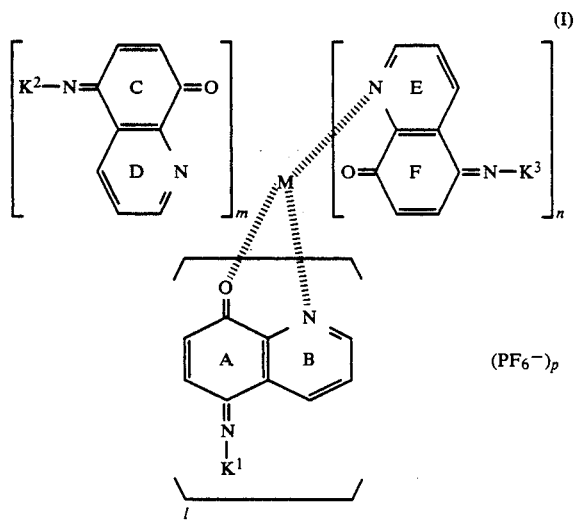

wherein M is a metal atom of Group VIII, Ib, IIb, IIIb, IVa, Va, VIa or VIIa of the Periodic Table or its halide or oxide, rings A, B, C, D, E and F may have substituents, each of $K^1$, $K^2$ and $K^3$ is a residue of a susbtituted or unsubstituted aromatic amine, each of l, m and n is 0 or 1, provided $l+m+n=2$ or 3, and p is 2, 3 or 4.

The present invention provides also an optical recording medium comprising a substrate and a recording layer containing a dye formed on the substrate wherein the recording is effected by irradiation of a laser beam to impart a thermal deformation of the recording layer and the reproduction is done by reading difference in the relectance between the deformed portion and the undeformed portion, wherein said dye is a metal-containing indoaniline compound of the formula I.

In the accompanying drawings:

FIG. 1 shows the visible range absorption spectrum of the metal-containing indoaniline compound of the present invention having $PF_6^-$ as a counter anion, as presented in Example 1. In this Figure, the ordinate represents the absorbance and the abscissa represents the wavelength (nm).

Figure 2:
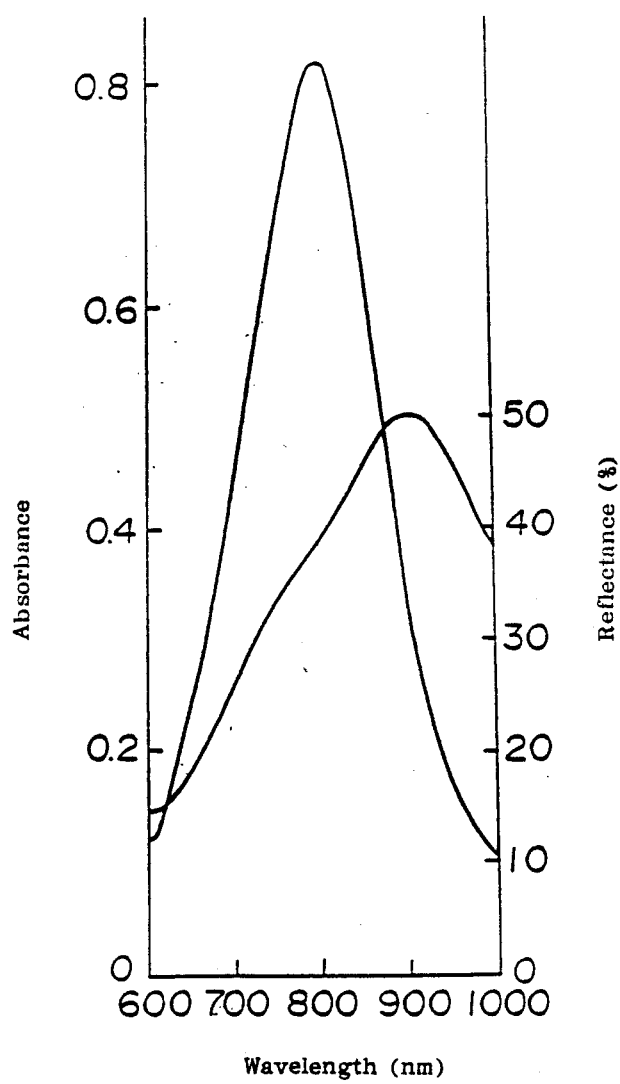

FIG. 2 shows the absorption spectrum and reflection spectrum of a thin coating layer of the metal-containing indoaniline compound of example 1. The ordinate at the left represents the absorbance and the ordinate at the right represents the relectance. The abscissa represents the wavelength (nm).

Now, the structure of the metal-containing indoaniline compound of the formula I will be described in detail.

In the formula I, the residue of a substituted or unsubstituted aromatic amine for $K^1$, $K^2$ and $K^3$ may be, for example, a residue of a heterocyclic amine containing a nitrogen atom, an oxygen atom or a sulfur atom such as a tetrahydroquinoline or a julolidine, or a group represented by the formula:

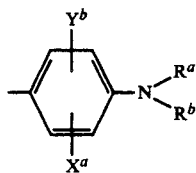

wherein each of $X^a$ and $Y^b$ is a hydrogen atom, an alkyl group, an acylamino group, an alkoxycarbonylamino group, an alkylsulfonylamino group, an alkoxy group or a halogen atom, and each of $R^a$ and $R^b$ is a hydrogen atom or a $C_{1-20}$ alkyl group, an aryl group, an alkenyl group or a cycloalkyl group, which may be substituted, or $R^a$ and $R^b$ may together form a ring via an oxygen atom, a nitrogen atom or a sulfur atom.

The substituents for the alkyl group, the aryl group, the alkenyl group or the cycloalkyl group for $R_a$ and $R_b$ may be, for example, an alkoxy group, an alkoxyalkoxy group, an alkoxyalkoxyalkoxy group, an allyoxy group, an aryl group, an aryloxy group, a cyano group, a nitro group, a hyroxyl group, a tetrahydrofuryl group, an alkylsulfonylamino group, an acyloxy group and a halogen atom. Further, as the substituents for the aryl group and the cycloalkyl group, an alkyl group or a vinyl group may be mentioned.

Among the compounds represented by the formula I, preferred are those represented by the formula:

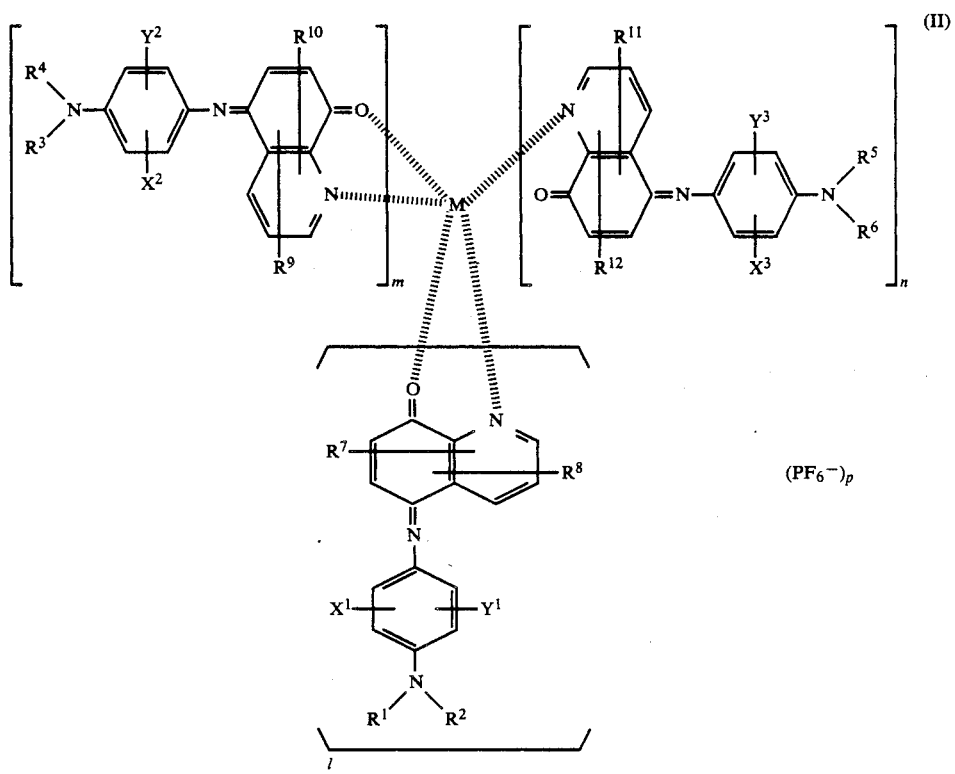

wherein M is a metal atom of Group VIII, Ib, IIb, IIIb, IVa, VA, VIa or VIIa of the Periodic Table, each of $R^7$, $R^8$, $R^9$, $R^{10}$, $R^{11}$, $R^{12}$, $X^1$, $X^2$, $X^3$, $Y^1$, $Y^2$ and $Y^3$ is a hydrogen atom, a halogen atom, an alkyl group, an alkoxy group, an acylamino group, an alkoxycarbonylamino group or an alkylsulfonylamino group, each of $R^1$, $R^2$, $R^3$, $R^4$, $R^5$ and $R^6$ is a hydrogen atom, a $C_{1-20}$ alkyl group, an aryl group, an alkenyl group or a cycloalkyl group, which may be substituted, each of 1, m and n is 0 or 1, provided $1+m+n=2$ or 3, and p is 2, 3 or 4.

Particularly preferred are those represented by the formula:

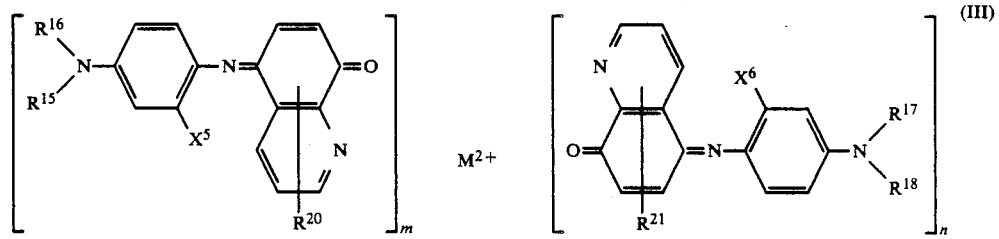

-continued

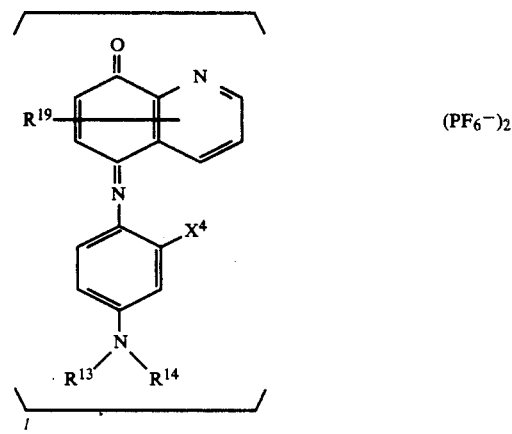

(PF$_6^-$)$_2$ wherein M is a metal atom of Ni, Cu, Co, Zn or Pe, each of X$^4$, X$^5$ and X$^6$ is a hydrogen atom or a C$_{1-4}$ alkyl group, each of R$^{13}$, R$^{14}$, R$^{15}$, R$^{16}$, R$^{17}$ and R$^{18}$ is a C$_{1-8}$ alkyl group, an alkoxyalkyl group, an alkoxyalkoxyalkyl group, an alkoxyalkoxyalkoxyalkyl group, an allyloxyalkyl group, an arylalkyl group, an aryloxyalkyl group, a cyanoalkyl group, a hydroxyalkyl group, a tetrahydrofurylalkyl group, an alkylsulfonylaminoalkyl group, an acyloxyalkyl group or an alkenyl group, each of R$^{19}$, R$^{20}$ and R$^{21}$ is a hydrogen atom, a C$_{1-4}$ alkyl group or a halogen atom, and each of l, m and n is 0 or 1, provided l+m+n=2 or 3.

Among them, especially preferred are those of the formula III wherein each of R$^{13}$, R$^{14}$, R$^{15}$ and R$^{16}$ is a C$_{1-6}$ alkyl group, each of R$^{19}$, R$^{20}$ and R$^{21}$ is a hydrogen atom or a C$_{1-4}$ alkyl group, and each of X$^4$, X$^5$ and X$^6$ is a C$_{1-4}$ alkyl group.

The novel metal-containing indoaniline compound of the formula I has an absorption in the wavelength range of from 600 to 900 nm, and a molecular absorption coefficient of as high as at least 10$^5$ cm$^{-1}$, and thus it has excellent characteristics suitable for an optical recording medium.

The metal-containing indoaniline compound of the formula I used in the present invention may be prepared, for example, by subjecting a compound of the formula:

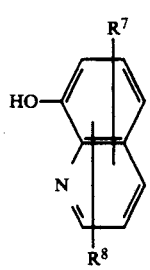

wherein R$^7$ and R$^8$ are as defined above, to oxidative condensation with a hydrochloride of a compound of the formula:

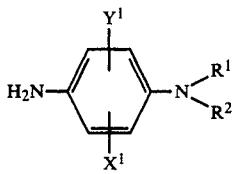

wherein X$^1$, Y$^1$, R$^1$ and R$^2$ are as defined above, to obtain a compound of the formula:

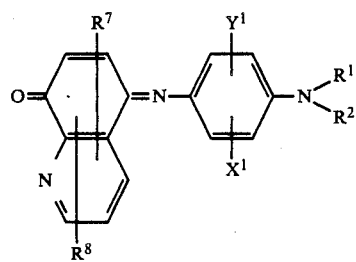

wherein R$^1$, R$^2$, R$^7$, R$^8$, X$^1$ and R$^1$ are as defined above, and then reacting the above compound with a compound of the formula:

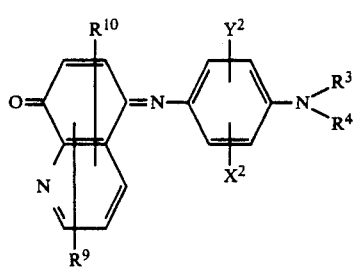

wherein R$^3$, R$^4$, R$^9$, R$^{10}$, X$^2$ and Y$^2$ are as defined above, and/or a compound of the formula:

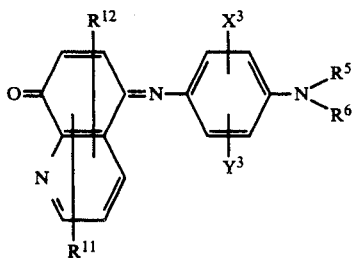

wherein $R^5$, $R^6$, $R^{11}$, $R^{12}$, $X^3$ and $Y^3$ are as defined above, and a compound of the formula:

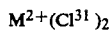

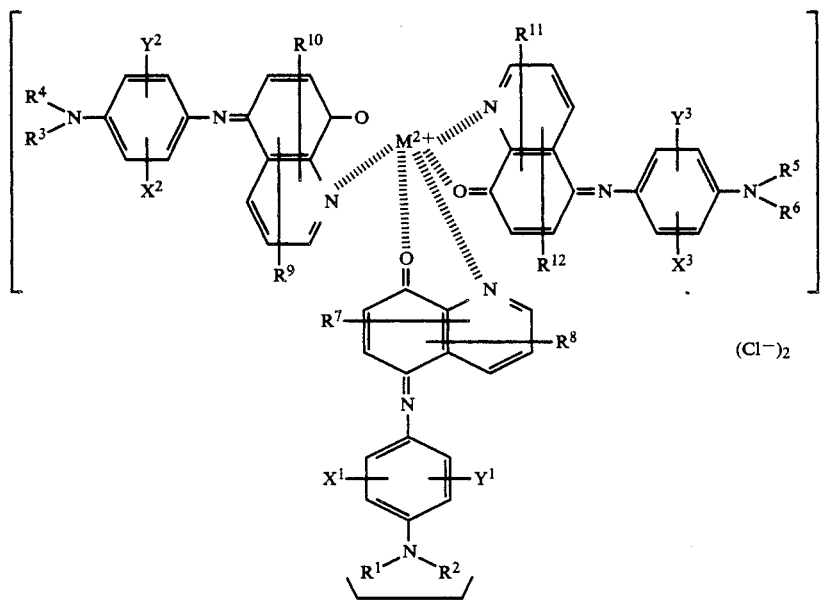

wherein $R^1$, $R^2$, $R^3$, $R^4$, $R^5$, $R^6$, $R^7$, $R^8$, $R^9$, $R^{10}$, $R^{11}$, $R^{12}$, $X^1$, $X^2$, $X^3$, $Y^1$, $Y^2$, $Y^3$ and M are as defined above, or a compound of the formula:

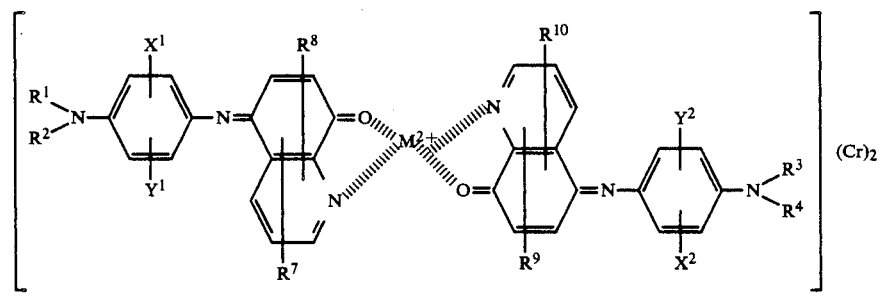

wherein $R^1$, $R^2$, $R^3$, $R^4$, $R^7$, $R^8$, $R^9$, $R^{10}$, $X^1$, $X^2$, $Y^1$, $Y_2$ and M are as defined above, and then reacting the above compound with a compound of the formula $NH_4PF_6$ (counter ion exchanger).

When the metal-containing indoaniline compound obtained by the above process is to be used for an optical recording medium of the present invention, the dye may be a single compound or a mixture of compounds having different substituents or different coordination numbers.

The optical recording medium of the present invention comprises essentially a substrate and a recording layer containing the metal-containing indoaniline compound. However, if necessary, an underlayer may be formed on the substrate, or a protective layer may be formed on the recording layer.

The substrate in the present invention may be transparent or opaque to the laser beam to be used. The substrate may be made of a material commonly used for a support for recording materials, such as glass, plastic, paper or a metal in a sheet or foil form. However, the plastic is most suitable from various viewpoints. The plastic includes an acrylic resin, a methacrylate resin, a vinyl acetate resin, a vinyl chloride resin, nitrocellulose, a polyethylene resin, a polypropylene resin, a polycarbonate resin, a polyimide resin, an epoxy resin and a polysulfone resin. Among them, an injection molded polycarbonate resin substrate is particularly preferred from the viewpoints of high productivity, costs and moisture resistance.

In the optical recording medium of the present invention, the recording layer containing the metal-containing indoaniline compound has a thickness of from 100 Å to 5 μm, preferably from 1,000 Å to 3 μm. The layer may be formed by employing a thin layer-forming method commonly employed, such as a vacuum vapor deposition method, a sputtering method, a doctor blade method, a casting method, a spinner method or a dipping method. If necessary, a binder may be employed. As such a binder, a conventional binder such as PVA, PVP, nitrocellulose, cellulose acetate, polyvinyl butyral or polycarbonate may be used. The weight ratio of the metal-containing indoaniline compound to the resin is preferably at least 1%. When the layer is formed by a spinner method, the rotational speed is preferably from 500 to 5,000 rpm. In some cases, after the spin coating, heat treatment or treatment with a solvent vapor may be applied.

Further, for the purpose of improving the stability or light-resistance of the recording medium, the recording layer may contain a transition metal chelate compound (such as acetyl acetonate chelate, bisphenyl dithiol, salicylaldehyde oxime or bisdithio-α-diketone) as a Singlet oxygen quencher.

Further, an additional dye may be incorporated. The additional dye may be a different compound of the same type or a dye of different type such as a triaryl methane dye, an azo dyestuff, a cyanine dye or squalerium dye.

When the recording layer is formed by a doctor blade method, a casting method, a spinner method or a dipping method, particularly by a coating method such as a spinner method, a solvent having a boiling point of from 120 to 160° C. such as tetrachloroethane, bromoform, dibromoethane, ethyl cellosolve, xylene, chlorobenzene or cyclohexanone is suitably employed as the solvent for coating.

Among them, a cellosolve solvent such as methyl cellosolve or ethyl cellosolve, or a ketone alcohol solvent such as diacetone alcohol or 3-hydroxy-3-methyl-2-butanone is particularly preferred since it can suitably be used without impairing the injection molded polycarbonate resin substrate which is preferred as the substrate.

The recording layer of the optical recording medium of the present invention may be provided on each side of the substrate, or on one side only.

Recording of information onto the recording medium thus obtained, is effected by irradiating a laser beam, preferably a semiconductor laser beam, collimated to have a diameter of about 1 μm onto the recording layer formed on each side or one sioe of the substrate. A thermal deformation such as the decomposition, evaporation or fusion due to the absorption of the laser energy takes place at the portions of the recording layer irradiated by the laser beam.

Reproduction of the recorded information is done by reading a difference in the reflectance between the portion where the thermal deformation occurred by the laser beam and the portion where no such thermal deformation took place.

The laser beam useful for the optical recording medium of the present invention includes a $N_2$ laser, a He-Cd laser, an Ar laser, a He-Ne laser, a rubby laser, a semiconductor laser and a color laser. A semiconductor laser is particularly preferred from the viewpoint of the light weight, easiness in handling and compact structure.

The metal-containing indoaniline compound having $PF_6^-$ as a counter anion of the present invention is excellent not only in the initial characteristics but also in the storage stability, whereby both properties are well balanced. Accordingly, an optical recording medium using such a compound is very useful.

Now, the present invention will be described in further detail with reference to Examples. However, it should be understood that the present invention is by no means restricted by such specific Examples.

The secondary distortion of the initial characteristics of the optical recording medium was calculated by the following equation.

Seconadry distortion (dB) = secondary harmonic carrier level - primary harmonic carrier level

EXAMPLE 1

(a) Preparation 1.07 g of a compound of the formula:

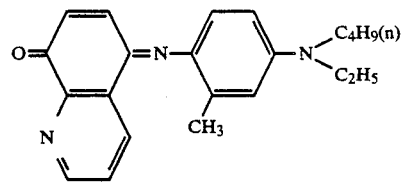

was dissolved in 500 ml of ethanol, and a solution of 0.44 g of $NiCl_2.6H_2O$ in 250 ml of water was added thereto. The mixture was stirred at room temperature for one hour. Then, a solution of 1.26 g of $NH_4PF_6$ in 250 ml of water was dropwise added thereto. Formed precipitates were collected by filtration under suction, washed with water and then dried to obtain 1.45 g (theoretical yield: 90%) of a metal-containing indoaniline compound of the formula:

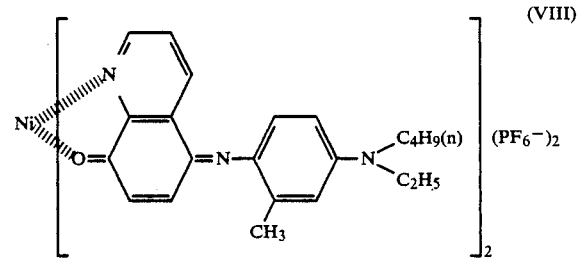

(VIII)

The visible range absorption spectrum (in Chloroform) of this compound was $\lambda_{max}$ 800 nm ($\epsilon_{max}$ 160000) as shown in FIG 1. The data obtained by TG-DSC show a heat generation initiating temperature of 186° C., whereby the heat generation peak was not sharp.

(b) Recording medium 0.15 g of the metal-containing indoaniline compound obtained in Preparation (a) was dissolved in 10 g of 3-hydroxy-3-methyl-2-butanone, and the solution was filtered through a filter of 0.22 μm to obtain a solution. 5 ml of this solution was dropped on an injection molded polycarbonate resin substrate (5 inches) with grooves having a depth of 700 Å and a width of 0.7 μm and coated by a spinner method at a rotational speed of 1,000 rpm. After coating, the coating layer was dried at 60° C. for 10 minutes. The coating layer had a maximum absorption wavelength of 810 nm and a reflectance of 42% (830 nm). The shape of the spectrum was broad.

FIG. 2 shows the absorbance and reflection spectrum of the coating layer.

(c) Optical recording

While rotating the above recording medium at a speed of 4 m/sec, a semiconductor laser beam having a central wavelength of 830 nm was irradiated with a pulse width of 500 nsec, whereby the C/N ratio was 55 dB at an output of 6 mW. The sensitivity was flat without depending on the thickness of the layer, and the initial characteristics were excellent with a secondary distortion of −40 dB. Yet, the storage stability (at 65° C. under a relative humidity of 80%) was excellent. Thus, it was excellent as an optical recording medium.

COMPARATIVE EXAMPLES 1-1 and 1-2

Metal-containing indoaniline compounds of the following formulas (X) and (XI) were respectively coated in the same manner as in Example 1 to prepare discs. Then, the initial characteristics (the dependency of sensitivity on the thickness of the recording layer, and the secondary distortion) and the storage stability (the change in the reflectance of the coating layer, and the change in the absorbancy of the dye powder) were evaluated and compared. As shown in Table 1, each of the discs prepared from these compounds was inferior in both properties to the optical recording medium of Example 1 of the present invention and was unsuitable as an optical recording medium with the properties being out of balance.

EXAMPLE 2

(a) Preparation 0.54 g of a compound of the formula:

and 0.56 g of a compound of the formula:

were dissolved in 500 ml of ethanol, and a solution of 0.44 g of NiCl$_2$.6H$_2$O in 100 ml of water was added thereto. The mixture was stirred at room temperature for one hour.

Then, a solution of 1.26 g of NH$_4$PF$_6$ in 100 ml of water was dropwise added thereto. Formed precipitates were collected by filtration under suction, washed with water and dried to obtain 1.44 g of a mixture of the metal-containing indoaniline compounds of the following formulas:

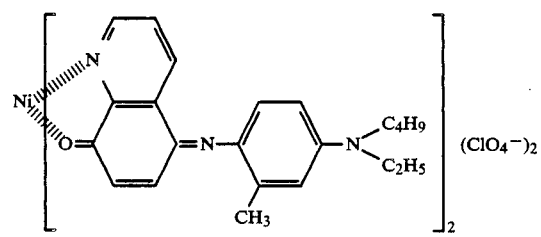

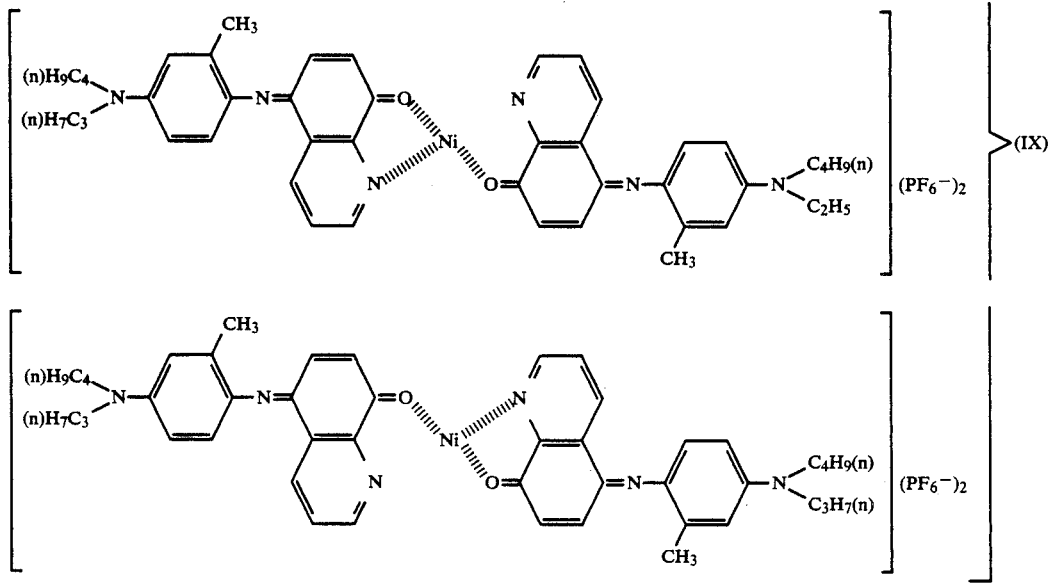

The visible region absorption spectrum (in chloroform) of this product was $\lambda_{max}$ 800 nm ($\epsilon_{max}$ 159000).

(b) Recording medium 0.15 g of the mixture of the metal-containing indoaniline compounds obtained in Preparation (a) was dissolved in 10 g of diacetone alcohol and filtered through a coil filter of 0.22 μm to obtain a solution. 5 ml of this solution was dropped on an injection molded polycarbonate resin substrate (5 inches) with grooves having a depth of 700 Å and a width of 0.7 μm and coated by a spinner method at a rotational speed of 700 rpm. After coating, the coating layer was dried at 60° C. for 10 minutes.

The maximum absorption wavelength of the coating layer was 810 nm, and the reflectance was 44% (830 nm). The shape of the spectrum was broader than that of a single compound.

(c) Optical recording

While rotating the above recording medium at a speed of 4 m/sec, a semiconductor laser beam with a central wavelength of 830 nm was irradiated with a pulse width of 500 nsec, whereby the C/N ratio was 54 dB at an output of 6 mW. The sensitivity was flat without depending on the thickness of the recording layer, and the initial characteristics were excellent with a secondary distortion of −42 dB. Yet, the storage stability (at 65° C. under a relative humidity of 80%) was excellent. Thus, the recording medium was excellent as an optical recording medium. These results are shown in Table 1.

COMPARATIVE EXAMPLES 2-1 and 2-2

The mixtures of metal-containing indoaniline compounds represented by the following formulas XII and XIII were respectively coated in the same manner as in Example 2 to prepare discs, and the initial characteristics (the dependency of sensitivity on the thickness of the recording layer, and the secondary distortion) and the storage stability (the change in the reflectance of the coating layer, and the change in the absorbance of the dye powder) were evaluated and compared. As shown in Table 1, each of the discs prepared from these mixtures was inferior in both properties to the optical recording medium of Example 2 of the present invention, and was unsuitable as an optical recording medium with the properties being out of balance.

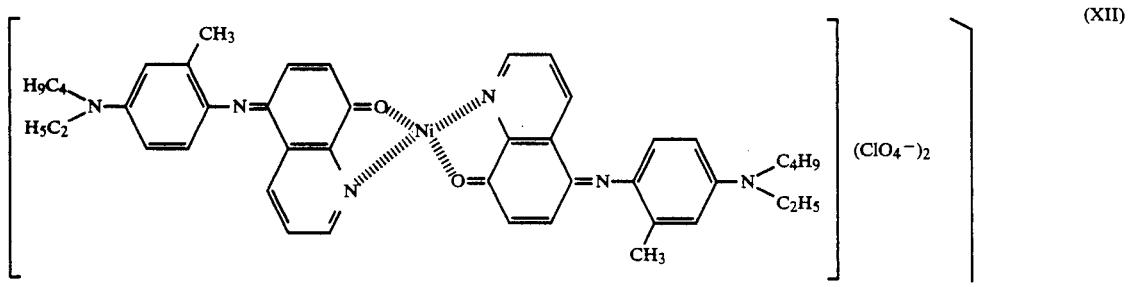

-continued
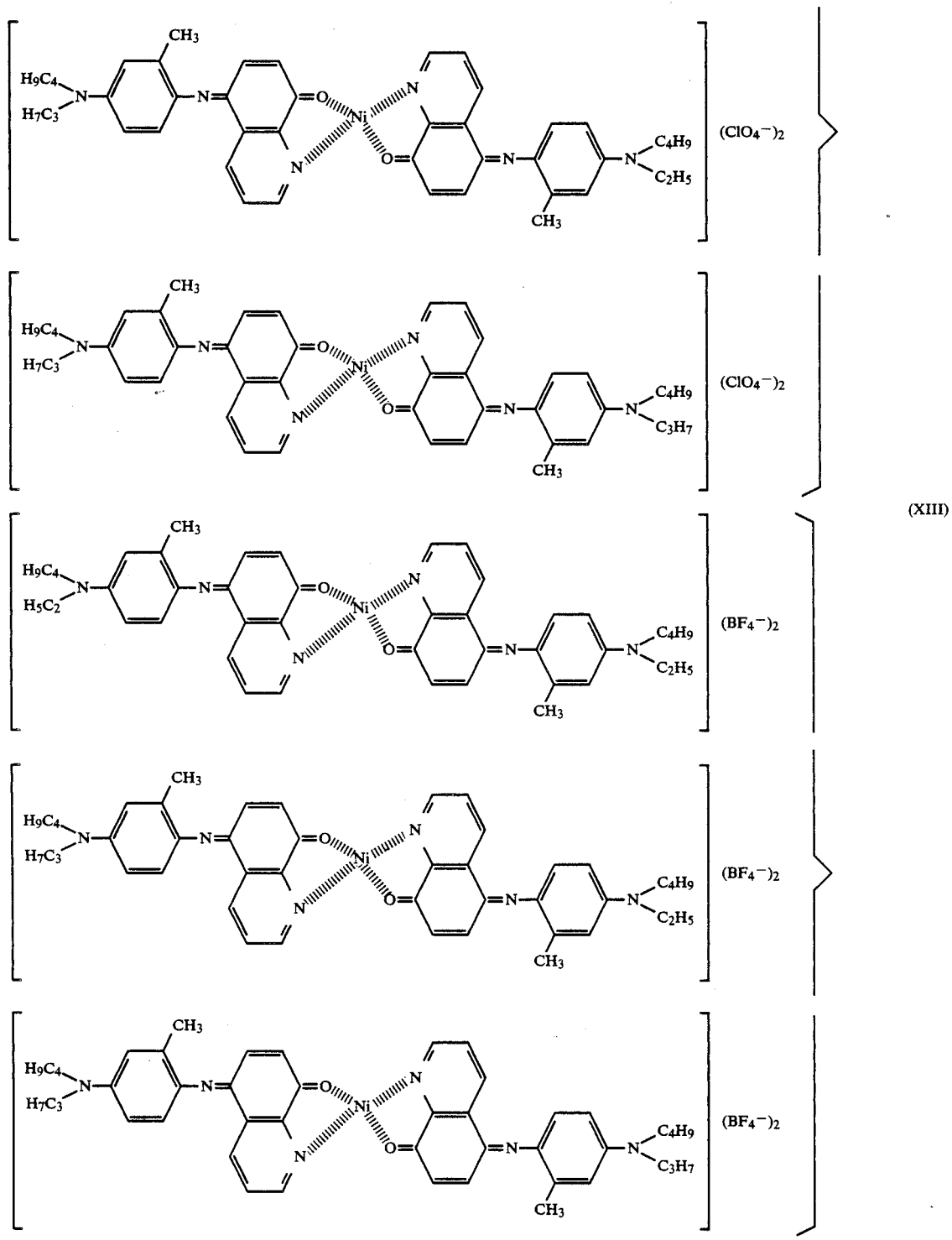
TABLE 1
| | Formula | Initial characteristics | | Storage stability (65° C., 80% RH, 500 hrs) | |
| | | Dependency of sensitivity of the thickness of the recording layer | Secondary distortion | Change in the reflectance of the coating layer | Change in the absorbance of the dye powder |
|---|---|---|---|---|---|
| Example 1 | (VIII) | Suitable (flat) | −40 dB | 2.3% | 1.1% |
| Comparative | (X) | Rather unsuitable | −30 dB | 5.0% | 4.2% |

TABLE 1-continued

| | Formula | Initial characteristics | | Storage stability (65° C., 80% RH, 500 hrs) | |
|---|---|---|---|---|---|
| | | Dependency of sensitivity of the thickness of the recording layer | Secondary distortion | Change in the reflectance of the coating layer | Change in the absorbance of the dye powder |
| Example 1-1 | | (abrupt increase) | | | |
| Comparative Example 1-2 | (XI) | Suitable (flat) | −40 dB | 25% | 20% |
| Example 2 | (IX) | Suitable (flat) | −42 dB | 0.9% | 0.8% |
| Comparative Example 2-1 | (XII) | Rather unsuitable (abrupt increase) | −28 dB | 4.4% | 4.1% |
| Comparative Example 2-2 | (XIII) | Suitable (flat) | −40 dB | 27% | 23% |

EXAMPLE 3

Instead of the dye employed in Example 1, each of the compounds identified in Table 2 was prepared and coated on a substrate in the same manner as in Example 1 to obtain a substrate having a thin coating layer with the maximum absorption wavelength as identified in Table 2. To the thin coating layer thus obtained, writing was conducted by means of a semiconductor laser as a light source, whereby pits of uniform and clear shapes were obtained. The sensitivity and the C/N ratio were excellent. The initial characteristics (the dependency of sensitivity on the thickness of the recording layer, and the secondary distortion) were excellent. Yet, the storage stability was excellent. Thus, it was excellent as an optical recording medium.

TABLE 2

$$\left[ M^{2+} \underset{N}{\overset{O=}{\diagdown}} \underset{R^x, R^y}{\overset{=N-K}{\diagup}} \right]_2 (PF_6^-)_2$$

| No. | M | $R^x$ | $R^y$ | K | Maximum absorption wavelength of the thin coating layer |
|---|---|---|---|---|---|
| 3-1 | Ni | H | H | —⟨ ⟩—N(C$_3$H$_7$(n))(C$_3$H$_7$(n)), CH$_3$ | 810 |
| 3-2 | ″ | ″ | ″ | —⟨ ⟩—N(C$_2$H$_5$)(C$_3$H$_7$(n)), CH$_3$ | 809 |
| 3-3 | Ni | H | H | —⟨ ⟩—N(C$_4$H$_9$(n))(C$_4$H$_9$(n)), CH$_3$ | 812 |
| 3-4 | ″ | ″ | ″ | —⟨ ⟩—N(C$_3$H$_7$(n))(C$_4$H$_9$(n)), CH$_3$ | 810 |

TABLE 2-continued $$\left[ M^{2+} \underset{N}{\overset{O}{\underset{R^x, R^y}{\bigwedge}}} \underset{4}{\overset{7}{\bigodot}} \underset{N-K}{\overset{8}{\bigodot}} \right]_2 (PF_6^-)_2$$

| No. | M | R$^x$ | R$^y$ | K | Maximum absorption wavelength of the thin coating layer |
|-----|---|-------|-------|---|---------------------------------------------------------|
| 3-5 | " | " | " | 3-CH$_3$-4-[N(C$_5$H$_{11}$(n))$_2$]phenyl | 812 |
| 3-6 | " | " | " | 3-CH$_3$-4-[N(C$_6$H$_{13}$(n))$_2$]phenyl | 813 |
| 3-7 | Ni | H | H | 4-[N(C$_3$H$_7$(n))$_2$]phenyl | 780 |
| 3-8 | " | " | " | 4-[N(C$_4$H$_9$(n))$_2$]phenyl | 782 |
| 3-9 | " | " | " | 4-[N(C$_5$H$_{11}$(n))$_2$]phenyl | 782 |
| 3-10 | " | " | " | 4-[N(C$_6$H$_{13}$(n))$_2$]phenyl | 783 |
| 3-11 | Ni | 2-CH$_3$ | H | 3-CH$_3$-4-[N(C$_4$H$_9$(n))$_2$]phenyl | 815 |
| 3-12 | " | " | " | 4-[N(C$_3$H$_7$(n))$_2$]phenyl | 782 |
| 3-13 | " | 6- or 7-Cl | " | 3-CH$_3$-4-[N(C$_2$H$_5$)$_2$]phenyl | 835 |

TABLE 2-continued $$\left[ M^{2+} \underset{N}{\overset{O}{\underset{|}{\bigvee}}} \underset{R^x, R^y}{\overset{7\ 8}{\bigvee}} =N-K \right]_2 (PF_6^-)_2$$

| No. | M | $R^x$ | $R^y$ | K | Maximum absorption wavelength of the thin coating layer |
|---|---|---|---|---|---|
| 3-14 | " | H | " | ![4-N(C2H5)2, 3-CH3 phenyl] | 808 |
| 3-15 | Ni | H | H | ![4-N(C2H5)2, 3-C2H5 phenyl] | 808 |
| 3-16 | " | " | " | ![4-N(C2H5)2, 3-C3H7(n) phenyl] | 808 |
| 3-17 | " | 6-CH$_3$ | " | ![4-N(C4H9(n))2, 3-CH3 phenyl] | 812 |
| 3-18 | " | H | " | ![3,4,5-tri-substituted phenyl with N(C4H9(n))2 and CH3 groups] | 812 |
| 3-19 | Ni | H | H | ![4-N(C4H9(n))2, 3-C4H9(n) phenyl] | 812 |
| 3-20 | Cu | " | " | ![4-N(C2H5)2, 3-CH3 phenyl] | 808 |
| 3-21 | Co | " | " | ![4-N(C4H9(n))2, 3-CH3 phenyl] | 808 |

TABLE 2-continued $$\left[ M^{2+} \underset{N}{\overset{O}{\underset{R^x, R^y}{\bigg|}}} \underset{4}{\overset{7}{\bigg|}} \overset{8}{=} N-K \right]_2 (PF_6^-)_2$$

| No. | M | $R^x$ | $R^y$ | K | Maximum absorption wavelength of the thin coating layer |
|---|---|---|---|---|---|
| 3-22 | Ni | 6- or 7-Cl | 2-CH$_3$ | aryl-N(C$_2$H$_5$)$_2$ with CH$_3$ | 840 |
| 3-23 | Cu | H | H | aryl-N(C$_4$H$_9$(n))$_2$ with CH$_3$ | 804 |
| 3-24 | " | " | " | aryl-N(C$_4$H$_9$(n))$_2$ with CH$_3$ | 784 |
| 3-25 | Fe | " | " | aryl-N(C$_3$H$_7$(i))(C$_2$H$_5$) with CH$_3$ | 802 |
| 3-26 | " | " | " | aryl-N(C$_3$H$_7$(n))$_2$ with CH$_3$ | 802 |
| 3-27 | Co | H | H | aryl-N(C$_2$H$_5$)$_2$ with CH$_3$ | 788 |
| 3-28 | " | " | " | aryl-N(C$_4$H$_9$(n))$_2$ with CH$_3$ | 790 |
| 3-29 | Cu | 6- or 7-Cl | 2-CH$_3$ | aryl-N(C$_4$H$_9$(n))$_2$ with CH$_3$ | 835 |

TABLE 2-continued
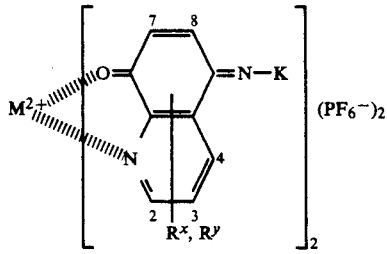
| No. | M | R$^x$ | R$^y$ | K | Maximum absorption wavelength of the thin coating layer |
|---|---|---|---|---|---|
| 3-30 | Co | H | " | 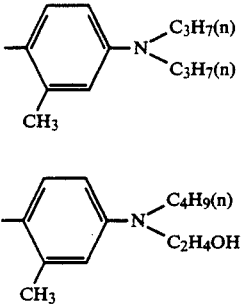 | 795 |
| 3-31 | Ni | H | H | 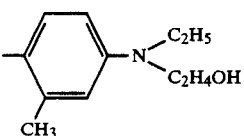 | 790 |
| 3-32 | " | " | " | 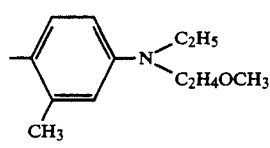 | 790 |
| 3-33 | " | " | " | 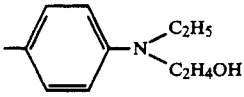 | 795 |
| 3-34 | " | " | " | 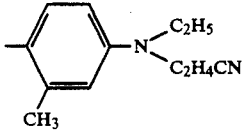 | 776 |
| 3-35 | Ni | H | H | 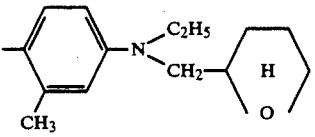 | 760 |
| 3-36 | " | " | " | 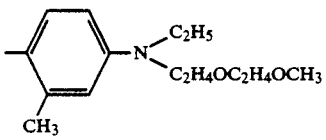 | 795 |
| 3-37 | " | " | " |  | 794 |

TABLE 2-continued $$\left[ M^{2+} \underset{N}{\overset{O}{\rightleftharpoons}} \underset{R^x, R^y}{\overset{7}{\rightleftharpoons}} \underset{4}{\overset{8}{\rightleftharpoons}} N-K \right]_2 (PF_6^-)_2$$

| No. | M | $R^x$ | $R^y$ | K | Maximum absorption wavelength of the thin coating layer |
|---|---|---|---|---|---|
| 3-38 | " | " | " | 4-methyl-3-methylphenyl-N(C2H5)(C2H4-phenyl) | 805 |
| 3-39 | Ni | H | H | 4-methyl-3-methylphenyl-N(C2H5)(C2H4O-phenyl) | 803 |
| 3-40 | " | " | " | 4-methyl-3-methylphenyl-N(C2H5)(C2H4OCH2CH=CH2) | 797 |
| 3-41 | " | " | " | 4-methyl-3-methylphenyl-N(C2H5)(C2H4NHSO3CH3) | 789 |
| 3-42 | " | " | " | 4-methyl-3-methylphenyl-N(C2H5)(C2H4OC2H4OC2H4OC2H6) | 795 |
| 3-43 | Ni | H | H | 4-methyl-3-methylphenyl-N(C2H4OCH3)(C2H4OCH3) | 788 |
| 3-44 | " | " | " | 4-methyl-3-methylphenyl-N(C2H4OH)(C2H4OH) | 776 |
| 3-45 | " | " | " | 4-methyl-3-methylphenyl-N(C2H5)(C2H4OC(=O)CH3) | 786 |

TABLE 2-continued $$\left[\underset{\underset{R^x, R^y}{\overset{2}{\bigvee}}\overset{3}{\underset{\phantom{X}}{\bigvee}}}{\overset{M^{2+}}{\underset{\phantom{X}N}{\overset{\phantom{X}}{\bigvee}}}}\overset{\overset{7}{\overset{8}{\phantom{X}}}}{\underset{\phantom{X}}{\overset{O}{\bigvee}}\overset{\phantom{X}}{\underset{\phantom{X}}{\overset{\phantom{X}}{\bigvee}}}\overset{\phantom{X}}{\underset{4}{\overset{\phantom{X}}{\bigvee}}}N-K}\right]_2 (PF_6^-)_2$$

| No. | M | $R^x$ | $R^y$ | K | Maximum absorption wavelength of the thin coating layer |
|---|---|---|---|---|---|
| 3-46 | " | " | " | 4-methyl-3-methylphenyl-N($C_2H_4OCH_3$)($C_2H_4OCCH_3$, =O) | 773 |
| 3-47 | Ni | H | H | 4-methyl-3-methylphenyl-N($C_2H_4OC_2H_4OC_2H_5$)($C_2H_4OC_2H_4OC_2H_5$) | 786 |
| 3-48 | " | " | " | 4-methyl-3-methylphenyl-N($C_2H_4OCCH_3$, =O)($C_2H_4OCCH_3$, =O) | 774 |
| 3-49 | " | " | " | 4-methyl-3-methylphenyl-N($C_2H_4OCH_3$)($C_2H_4OC_2H_4OCH_3$) | 785 |
| 3-50 | " | " | " | 4-methyl-3-methylphenyl-N($C_2H_4OCH_2CH=CH_2$)($C_2H_4OCH_2CH=CH_2$) | 786 |
| 3-51 | Ni | H | H | 4-methyl-3-NHCOCH$_3$-phenyl-N($C_2H_5$)($C_2H_5$) | 815 |
| 3-52 | " | " | " | 4-methyl-3-NHCOCH$_3$-phenyl-N($C_4H_9(n)$)($C_4H_9(n)$) | 816 |
| 3-53 | " | " | " | 4-methyl-3-NHCOCH$_3$-phenyl-N($C_4H_9(n)$)($C_2H_4OH$) | 802 |

TABLE 2-continued $$\left[ \begin{array}{c} \text{M}^{2+} \cdots \text{O} \\ \text{N} \end{array} \begin{array}{c} 7 \quad 8 \\ \\ 2 \quad 3 \\ R^x, R^y \end{array} \text{N}-\text{K} \right]_2 (PF_6^-)_2$$

| No. | M | $R^x$ | $R^y$ | K | Maximum absorption wavelength of the thin coating layer |
|---|---|---|---|---|---|
| 3-54 | " | " | " | 4-methyl-N,N-bis(2-methoxyethyl)-3-(acetylamino)aniline group | 808 |
| 3-55 | Ni | H | H | 4-methyl-N,N-diethyl-3-(ethoxycarbonylamino)aniline group | 801 |
| 3-56 | " | " | " | 4-methyl-N,N-diethyl-3-(benzoylamino)aniline group | 798 |
| 3-57 | " | " | " | 4-methyl-N,N-diethyl-3-(ethylsulfonylamino)aniline group | 799 |
| 3-58 | " | " | " | 2-methoxy-4,6-dimethyl-5-(N,N-diethylamino)phenyl group | 814 |
| 3-59 | Ni | H | H | 2-chloro-4-methyl-5-(N,N-diethylamino)-(acetylamino)aniline group | 805 |
| 3-60 | " | " | " | 2-chloro-4-methyl-5-(N-butylamino)-(acetylamino)aniline group | 732 |

TABLE 2-continued $$\left[ \begin{array}{c} \text{structure with } M^{2+}, O, N, K, \text{ positions } 2,3,4,7,8 \text{ and } R^x, R^y \end{array} \right]_2 (PF_6^-)_2$$

| No. | M | $R^x$ | $R^y$ | K | Maximum absorption wavelength of the thin coating layer |
|---|---|---|---|---|---|
| 3-61 | " | " | " | ![4-OCH₃, 5-N(C₂H₅)₂, 2-NHCOCH₃ phenyl] | 829 |
| 3-62 | " | " | " | ![4-OCH₃, 5-N(C₂H₅)₂, 2-OCH₃ phenyl] | 807 |
| 3-63 | Ni | H | H | ![5-N(C₅H₁₁(n))₂, 2-NHCOCH₃ phenyl] | 817 |
| 3-64 | " | " | " | ![5-N(C₃H₇(n))₂, 2-NHCOCH₃ phenyl] | 816 |
| 3-65 | " | " | " | ![5-N(C₂H₅)₂, 2-NHCOOCH₃ phenyl] | 800 |
| 3-66 | " | " | " | ![5-N(C₂H₅)₂, 2-NHCOOC₃H₇(n) phenyl] | 800 |
| 3-67 | Ni | H | H | ![morpholino-tolyl with CH₃] | 788 |
| 3-68 | " | " | " | ![piperazinyl-tolyl with CH₃, NH] | 790 |

TABLE 2-continued $$\left[\begin{array}{c} \text{structure with } M^{2+}, O, N, N-K, R^x, R^y \text{ at positions 2,3,4,7,8} \end{array}\right]_2 (PF_6^-)_2$$

| No. | M | $R^x$ | $R^y$ | K | Maximum absorption wavelength of the thin coating layer |
|---|---|---|---|---|---|
| 3-69 | " | 4-CH$_3$ | 6-CH$_3$ | aryl-N(C$_4$H$_9$(n))(C$_4$H$_9$(n)) with 4-CH$_3$ | 812 |
| 3-70 | " | " | " | aryl-N(C$_2$H$_5$)(C$_2$H$_5$) with CH$_3$ and C$_2$H$_5$ substituents | 808 |

Table 3 shows specific examples of the metal-containing indoaniline compounds which can suitably be used for the optical recording medium of the present invention in addition to the compounds used in the preceding Examples.

TABLE 3

$$\left[\begin{array}{c} \text{structure with } M^{2+}_n, O, N, N-K, R^x, R^y \text{ at positions 2,3,4,6,7} \end{array}\right]_2 (PF_5^-)_2$$

| M | $R^x$ | $R^y$ | K |
|---|---|---|---|
| Ni | H | H | aryl-N(CH$_2$CH=CH$_2$)(C$_2$H$_5$), with CH$_3$ |
| " | " | " | aryl-N(CH$_2$CH=CH$_2$)(CH$_2$CH=CH$_2$), with CH$_3$ |
| " | " | " | aryl-N(CH$_2$CF$_3$)(C$_4$H$_9$(n)), with CH$_3$ |

TABLE 3-continued $$\left[\begin{array}{c} \text{structure with } M^{2+}_n, O, N, N-K, R^x, R^y \text{ at positions 2,3,4,6,7} \end{array}\right]_2 (PF_5^-)_2$$

| M | $R^x$ | $R^y$ | K |
|---|---|---|---|
| " | " | 7-OCH$_3$ | aryl-N(C$_4$H$_9$(n))(C$_4$H$_9$(n)), with CH$_3$ |
| Ni | H | 7-NHCOCH$_3$ | aryl-N(C$_4$H$_9$(n))(C$_4$H$_9$(n)), with CH$_3$ |
| " | " | 6-NHCOCH$_3$ | aryl-N(C$_4$H$_9$(n))(C$_4$H$_9$(n)), with CH$_3$ |
| " | " | 7-NHCOOC$_2$H$_5$ | aryl-N(C$_4$H$_9$(n))(C$_4$H$_9$(n)), with CH$_3$ |

TABLE 3-continued

[Structure: complex with M²⁺ coordinated to O and N of a fused ring system with positions 2,3,4,6,7 labeled, R^x, R^y substituents, =N—K group] (PF₅⁻)₂, subscript 2

| M | R^x | R^y | K |
|---|-----|-----|---|
| " | 2-CH₃ | 4-CH₃ | 4-methyl-3-methyl-phenyl-N(C₄H₉(n))₂ |
| Pd | H | H | 4-methyl-3-methyl-phenyl-N(C₄H₉(n))₂ |
| Zn | " | " | 4-methyl-3-methyl-phenyl-N(C₄H₉(n))₂ |
| Ti | H | H | 4-methyl-3-methyl-phenyl-N(C₄H₉(n))₂ |
| Fe | " | " | 4-methyl-3-methyl-phenyl-N(C₄H₉(n))₂ |
| VO | " | " | 4-methyl-3-methyl-phenyl-N(C₄H₉(n))₂ |
| Cr | " | " | 4-methyl-3-methyl-phenyl-N(C₄H₉(n))₂ |
| Pt | " | " | 4-methyl-3-methyl-phenyl-N(C₄H₉(n))₂ |

TABLE 3-continued

| M | R^x | R^y | K |
|---|-----|-----|---|
| Ni | " | " | 4-methyl-3-CF₃-phenyl-N(C₄H₉(n))₂ |
| Ni | H | H | 4-methyl-3-Cl-phenyl-N(C₄H₉(n))₂ |
| " | " | 7-CN | 4-methyl-3-methyl-phenyl-N(C₄H₉(n))₂ |
| " | " | 7-NO₂ | 4-methyl-3-methyl-phenyl-N(C₄H₉(n))₂ |
| Mn | " | H | 4-methyl-3-methyl-phenyl-N(C₄H₉(n))₂ |
| Ni | " | " | 6-substituted-1,2,3,4-tetrahydroquinoline, N-C₄H₉(n) |
| " | " | " | 6-methyl-4-methyl-2,2-dimethyl-1,2,3,4-tetrahydroquinoline, N-C₄H₉(n) |
| Ni | H | H | 6-methyl-7-methyl-4-methyl-2,2-dimethyl-1,2,3,4-tetrahydroquinoline, N-C₄H₉(n) |

TABLE 3-continued

[Structure: M²⁺ complex with substituted indoaniline, (PF₅⁻)₂, positions labeled 2,3,4,6,7 with Rˣ, Rʸ]

| M | Rˣ | Rʸ | K |
|---|----|----|---|
| " | " | " | [julolidine-type structure] |
| " | " | " | [thiophene with CN and N(C₄H₉(n))₂] |
| " | " | " | [pyridine with CH₃, CN, NH—C₄H₉(n), NHC₄H₉(n)] |
| " | " | " | [thiazoline-type with N, S, N(C₄H₉(n))₂] |

TABLE 3-continued

[Same structure: M²⁺ complex with (PF₅⁻)₂]

| M | Rˣ | Rʸ | K |
|---|----|----|---|
| " | " | " | [structure with N, S, two C₄H₉(n) groups] |

EXAMPLE 4

Instead of the mixture of the metal-containing indoaniline compounds used in Example 2, a mixture of metal-containing indoaniline compounds (counter anion being (PF₆-)₂) was prepared in the same manner as in Example 2 except that the metal salts represented by Example 2 compounds A, B and M shown in Table 4 were used, and coated on a substrate to obtain a substrate having a thin coating layer with the maximum absorption wavelength as shown in Table 4. To the thin coating layer thus obtained, writing was conducted by means of a semiconductor laser as a light source, whereby pits of uniform and clear shapes were obtained. The C/N ratio was excellent, and the storage stability was excellent.

TABLE 4

A: [indoaniline structure with O, =N—Kᵃ, positions 2,3,4,7,8, R°,Rᵖ]
B: [indoaniline structure with O, =N—Kᵇ, positions 2,3,4,7,8, Rᵠ,Rʳ]

| No. | M | R° | Rᵖ | Kᵃ | Rᵠ | Rʳ | Kᵇ | Maximum absorption wavelength of the thin coating layer (nm) |
|-----|---|----|----|----|----|----|----|------|
| 4-1 | Ni | H | H | [phenyl with CH₃, N(C₂H₅)₂] | H | H | [phenyl with CH₃, N(C₃H₇(n))₂] | 810 |
| 4-2 | " | " | " | " | " | " | [phenyl with CH₃, N(C₄H₉(n))(C₃H₇(n))] | " |

TABLE 4-continued
A: 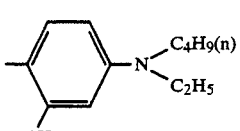   B: 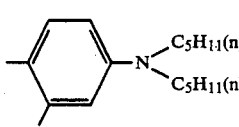
| No. | M | A R$^o$ | R$^p$ | K$^a$ | B R$^q$ | R$^r$ | K$^b$ | Maximum absorption wavelength of the thin coating layer (nm) |
|---|---|---|---|---|---|---|---|---|
| 4-3 | " | " | " | " | " | " | 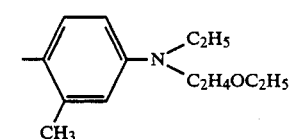 | " |
| 4-4 | " | " | " | " | " | " | 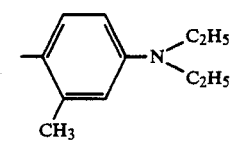 | " |
| 4-5 | " | " | " | " | " | " | 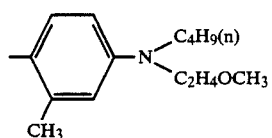 | 808 |
| 4-6 | Ni | H | H | 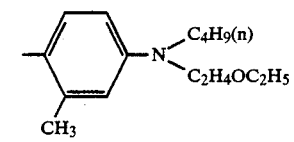 | H | H | 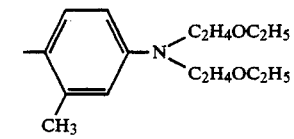 | 808 |
| 4-7 | " | " | " | " | " | " | 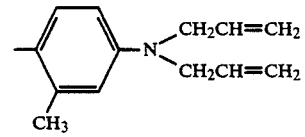 | " |
| 4-8 | " | " | " | " | " | " | 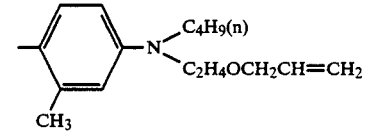 | 806 |
| 4-9 | " | " | " | " | " | " |  | 805 |
| 4-10 | " | " | " | " | " | " |  | 807 |

TABLE 4-continued $$A: \left\{\begin{array}{c}\text{quinone-imine structure with positions 2,3,4,7,8, N ring, } R^o, R^p, \text{ and } =N-K^a\end{array}\right\}$$

$$B: \left\{\begin{array}{c}\text{quinone-imine structure with positions 2,3,4,7,8, N ring, } R^q, R^r, \text{ and } =N-K^b\end{array}\right\}$$

| No. | M | A $R^o$ | $R^p$ | $K^a$ | B $R^q$ | $R^r$ | $K^b$ | Maximum absorption wavelength of the thin coating layer (nm) |
|---|---|---|---|---|---|---|---|---|
| 4-11 | " | " | " | " | " | " | 4-methyl-3-methylphenyl-N(C$_6$H$_{13}$(n))(C$_6$H$_{13}$(n)) | 812 |
| 4-12 | " | " | " | 4-methyl-3-methylphenyl-N(C$_2$H$_5$)(C$_2$H$_4$OC$_2$H$_5$) | " | " | 4-methyl-3-methylphenyl-N(C$_4$H$_9$(n))(C$_2$H$_4$OH) | 805 |
| 4-13 | Ni | H | H | 4-methyl-3-methylphenyl-N(C$_2$H$_5$)(C$_2$H$_5$) | H | H | 4-methyl-3-methylphenyl-N(C$_2$H$_5$)(C$_2$H$_4$CN) | 770 / 800 |
| 4-14 | " | " | " | " | " | " | 4-methyl-3-methylphenyl-N(C$_2$H$_5$)(CH$_2$-CH(CH)(O)-...tetrahydropyranyl) | 808 |
| 4-15 | " | " | " | " | " | " | 4-methyl-3-methylphenyl-N(C$_2$H$_5$)(CH$_2$-C$_6$H$_5$) | 800 |
| 4-16 | " | " | " | " | " | " | 4-methyl-3-methylphenyl-N(C$_4$H$_9$(n))(C$_2$H$_4$-C$_6$H$_5$) | 809 |
| 4-17 | " | " | " | " | " | " | 4-methyl-3-methylphenyl-N(C$_2$H$_5$)(C$_2$H$_4$-O-C$_6$H$_5$) | " |
| 4-18 | " | " | " | " | " | " | 4-methyl-3-methylphenyl-N(C$_2$H$_5$)((C$_2$H$_4$O)$_2$C$_2$H$_5$) | 808 |

TABLE 4-continued

A: [structure with O=, N—K^a, positions 7,8,2,3,4, R^o,R^p]  B: [structure with O=, N—K^b, positions 7,8,2,3,4, R^q,R^r]

| No. | M | A R^o | R^p | K^a | B R^q | R^r | K^b | Maximum absorption wavelength of the thin coating layer (nm) |
|---|---|---|---|---|---|---|---|---|
| 4-19 | " | " | " | " | " | " | [4-methyl-3-methylphenyl-N(C2H5)(C2H4O)3C2H5] | " |
| 4-20 | Ni | H | H | [4-methyl-3-methylphenyl-N(C2H5)2] | H | H | [4-methyl-3-methylphenyl-N(C2H5)(C2H4NHSO2CH3)] | 800 |
| 4-21 | " | " | " | " | " | " | [4-methyl-3-methylphenyl-N(C2H5)(C2H4OCOCH3)] | 792 |
| 4-22 | " | " | " | " | " | " | [4-methylphenyl-N(C2H5)2] | 800 |
| 4-23 | " | " | " | " | " | " | [4-methylphenyl-N(C4H9(n))2] | " |
| 4-24 | " | " | " | " | " | " | [4-methylphenyl-N(C3H7(n))2] | " |
| 4-25 | Cu | " | " | " | " | " | [4-methyl-3-methylphenyl-N(C4H9(n))2] | " |
| 4-26 | Co | " | " | " | " | " | " | 788 |
| 4-27 | Zn | H | H | [4-methyl-3-methylphenyl-N(C2H5)2] | H | H | [4-methyl-3-methylphenyl-N(C4H9(n))2] | 810 |

TABLE 4-continued

A:
$$\left\{ \begin{array}{c} \includegraphics \end{array} \right\}$$

B:
$$\left\{ \begin{array}{c} \includegraphics \end{array} \right\}$$

(Structures showing indoaniline core with positions 2,3,4,7,8, N, =N—K$^a$ / =N—K$^b$, and R$^o$,R$^p$ / R$^q$,R$^r$)

| No. | M | A R$^o$ | R$^p$ | K$^a$ | B R$^q$ | R$^r$ | K$^b$ | Maximum absorption wavelength of the thin coating layer (nm) |
|---|---|---|---|---|---|---|---|---|
| 4-28 | Ni | " | " | —C$_6$H$_3$(CH$_3$)—N(C$_4$H$_9$(n))$_2$ | " | " | —C$_6$H$_3$(CH$_3$)—N(C$_4$H$_9$(n))(C$_3$H$_7$(n)) | " |
| 4-29 | " | " | " | " | " | " | —C$_6$H$_3$(CH$_3$)—N(C$_4$H$_9$(n))(C$_5$H$_{11}$(n)) | " |
| 4-30 | " | " | " | " | " | " | —C$_6$H$_3$(CH$_3$)—N(C$_6$H$_{13}$(n))$_2$ | " |

EXAMPLE 5

(a) Preparation 1.07 g of a compound of the formula:

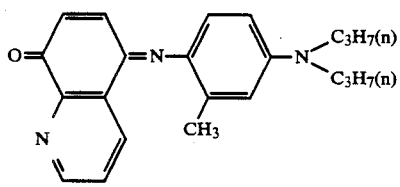

was dissolved in 500 ml of ethanol. Then, a solution of 0.36 g of NiC$_{12}$.6H$_2$O in 100 ml of water and a solution of 1.26 g of NH$_4$PF$_6$ in 100 ml of water were mixed and dropwise added thereto over a period of about one hour. The mixture was stirred at room temperature for one hour. Then, 100 ml of water was added thereto, and the mixture was stirred at room temperature for 2 hours. Formed precipitation were collected by filtration under suction, washed with water and dried to obtain 0.70 g of a metal-containing indoaniline compound of the formula:

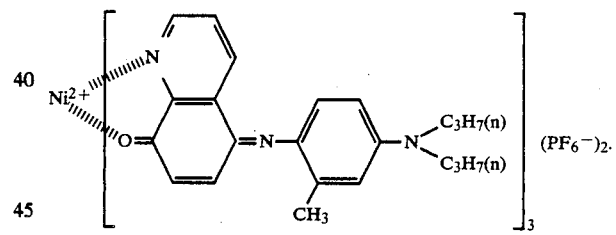

The visible range absorption spectrum (in chloroform) of this compound was $\lambda_{max}$ 801 nm ($\epsilon_{max}$ 200000).

The analytical values obtained by the elemental analysis of this compound are as shown below, which are in good agreement with the calculated values.

|  | C (%) | H (%) | N (%) |  |
|---|---|---|---|---|
| Calculated values (%) | 56.99 | 5.43 | 9.06 | (C$_{10}$H$_{75}$N$_9$O$_3$P$_2$F$_{12}$Ni) |
| Analytical values (%) | 56.83 | 5.51 | 8.76 | |

(b) Recording medium 0.17 g of the metal-containing indoaniline compound obtained in Preparation (a) was dissolved in 10 g of 3-hydroxy-3-methyl-2-butanone, and the solution was filtered through a filter of 0.22 μm to obtain a solution. 3 ml of this solution was dropped on an injection molded polycarbonate resin substrate (5 inches) with grooves having a depth of 650 Å and a width of 0.7 μm and coated by a spinner method at a rotational speed of 700 rpm. After coating, the coating layer was dried at 60° C. for 10 minutes. The coating layer had a maximum absorption wavelength of 800 nm and a reflectance of 40% (830 nm). The shape of the spectrum was broad.

(c) Optical recording

While rotating the above recording medium at a speed of 4 m/sec, a semiconductor laser beam having a central wavelength of 830 nm was irradiated with a pulse width of 500 nsec, whereby the C/N ratio was 56 dB at an output of 6 mW. The sensitivity was flat without depending on the thickness of the layer, and the initial characteristics were excellent with a secondary distortion of −40 dB. Yet, the storage stability (at 65° C. under a relative humidity of 80%) was excellent. Thus, it was excellent as an optical recording medium.

EXAMPLE 6

(a) Preparation 1.16 g of a compound of the formula:

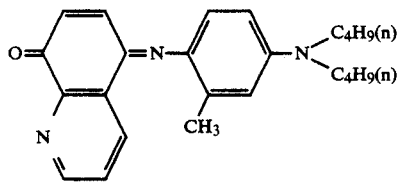

was dissolved in 500 ml of ethanol, and a solution of 0.44 g of $NiCl_2.6H_2O$ in 100 ml of water was added thereto. The mixture was stirred at room temperature for about one hour. Then, a solution of 1.26 g of $NH_4PF_6$ in 100 ml of water was dropwise added thereto, and the mixture was stirred at room temperature for one hour. Then, 100 ml of water was added thereto, and the mixture was stirred for 2 hours. Formed precipitates were collected by filtration under suction, washed with water and dried to obtain 1.20 g of a metal-containing indoaniline compound of the formula:

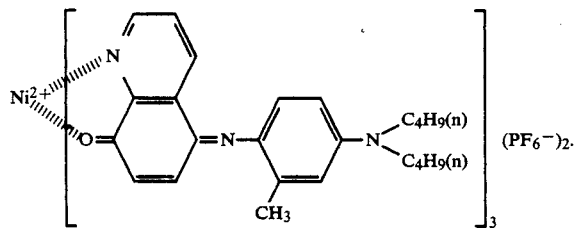

The visible range absorption spectrum (in chloroform) of this compound was $\lambda_{max}$ 803 nm ($\epsilon_{max}$ 200000).

The analytical values obtained by the elemental analysis of this compound are shown below, which are in good agreement with the calculated values.

|  | C (%) | H (%) | N (%) |  |
|---|---|---|---|---|
| Calculated values (%) | 58.62 | 5.94 | 8.54 | $(C_{72}H_{87}N_9O_3P_2F_{12}Ni)$ |
| Analytical values (%) | 58.58 | 5.95 | 8.54 |  |

(b) Recording medium 0.16 g of the metal-containing indoaniline compound obtained in Preparation (a) was dissolved in 10 g of 3-hydroxy-3-methyl-2-butanone, and the solution was filtered through a filter of 0.22 μm to obtain a solution. 5 ml of this solution was dropped on an injection molded polycarbonate resin substrate (5 inches) with grooves having a depth of 700 Å and a width of 0.7 μm and coated by a spinner method at a rotational speed of 800 rpm. After coating, the coated substrate was dried at 60° C. for 10 minutes. The coated layer had a maximum absorption wavelength of 805 nm and a reflectance of 38% (830 nm). The shape of the spectrum was broad.

(c) Optical recording

While rotating the above recording medium at a speed of 4 m/sec, a semiconductor laser beam having a central wavelength of 830 nm was irradiated with a pulse width of 500 nsec, whereby the C/N ratio was 55 dB at an output of 6 mW. The sensitivity was flat without depending on the thickness of the layer, and the initial characteristics were excellent with a secondary distortion of −41 dB. Yet, the storage stability (at 65° C. under a relative humidity of 80%) was excellent. Thus, it was excellent as an optical recording medium.

EXAMPLE 7

(a) Preparation 0.99 g of a compound of the formula:

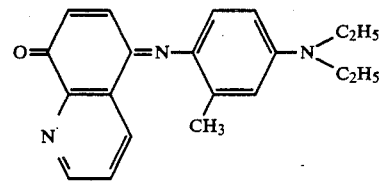

was dissolved in 500 ml of ethanol, and a solution of 0.44 g of $CoCl_2.6H_2O$ in 100 ml of water was added thereto. The mixture was stirred at room temperature for one hour. Then, a solution of 1.26 g of $NH_4PF_6$ in 100 ml of water was dropwise added thereto. Then, 100 ml of water was added, and formed precipitates were collected by filtration under suction, washed with water and dried to obtain 1.05 g of a metal-containing indoaniline compound of the formula:

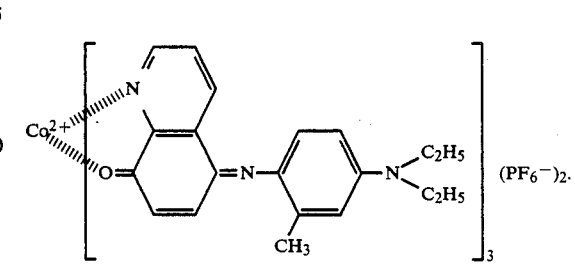

The visible range absorption spectrum (in chloroform) of this compound was $\lambda_{max}$ 802 nm ($\epsilon_{max}$ 185000).

The analytical values obtained by the elemental analysis of this compound are shown below, which are in good agreement with the calculated values.

|  | C (%) | H (%) | N (%) |  |
|---|---|---|---|---|
| Calculated values (%) | 55.14 | 4.85 | 9.64 | $(C_{60}H_{63}N_9O_3P_2F_{12}Ni)$ |
| Analytical values (%) | 55.43 | 4.90 | 9.58 |  |

(b) Recording medium 0.15 g of the mixture of the metal-containing indoaniline compounds obtained in Preparation (a) was dissolved in 10 g of diacetone alcohol filtered through a filter of 0.22 μm to obtain a solution. 5 ml of this solution was then dropped on an injection molded polycarbonate resin substrate (5 inches) with grooves having a depth of 700 Å and a width of 0.7 μm and coated by a spinner method at a rotational speed of 700 rpm. After coating, the coating layer was dried at 60° C. for 10 minutes. The coating layer had a maximum absorption wavelength of 806 nm and a reflectance of 36% (830 nm). The shape of the spectrum was broad.

(c) Optical recording

While rotating the above recording medium at a speed of 4 m/sec, a semiconductor laser beam having a central wavelength of 830 nm was irradiated with a pulse width of 500 nsec, whereby the C/N ratio was 54 dB at an output of 6 mW. The sensitivity was flat without depending on the thickness of the layer, and the initial characteristics were excellent with a secondary distortion of −42 dB. Yet, the storage stability (at 65° C. under a relative humidity of 80%) was excellent. Thus, it was excellent as an optical recording medium.

EXAMPLE 8

(a) Preparation 1.07 g of a compound of the formula:

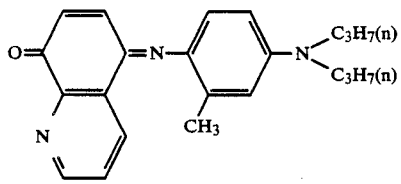

was dissolved in 500 ml of ethanol, and a solution of 6.6 g of $NiCl_2.6H_2O$ in 100 ml of water was added thereto. The mixture was stirred at room temperature for one hour. Then, a solution of 1.26 g of $NH_4PF_6$ in 100 ml of water was dropwise added thereto, and the mixture was stirred at room temperature for about 2 hours. Then, 100 ml of water was added thereto, whereby precipitates were formed. The stirring was continued in the suspended state for about one hour. Formed precipitates were collected by filtration under suction, washed with water and dried to obtain 0.82 g of a mixture of the metal-containing indoaniline compounds of the formula:

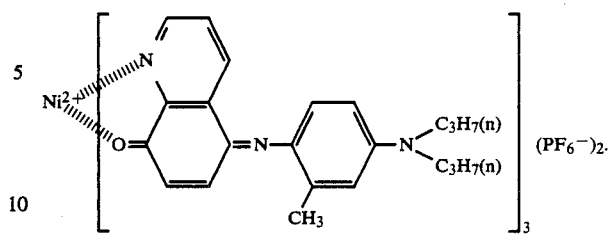

The visual region absorption spectrum in chloroform of this product was $\lambda_{max}$800 nm ($\epsilon_{max}$180000).

(b) Recording medium 0.15 g of the metal-containing indoaniline compound obtained in Preparation (a) was dissolved in 10 g of diacetone alcohol, and the solution was filtered through a filter of 0.22 μm to obtain a solution. 5 ml of this solution was dropped on an injection molded polycarbonate resin substrate (5 inches) with grooves having a depth of 700 Å and a width of 0.7 μm and coated by a spinner method at a rotational speed of 700 rpm. After coating, the coating layer was dried at 6020 C. for 10 minutes. The coating layer had a maximum absorption wavelength of 803 nm and a reflectance of 40% (830 nm). The shape of the spectrum was broad.

(c) Optical recording

While rotating the above recording medium at a speed of 4 m/sec, a semiconductor laser beam having a central wavelength of 830 nm was irradiated with a pulse width of 500 nsec, whereby the C/N ratio was 53 dB at an output of 6 mW. The storage stability (at 65° C. under a relative humidity of 80%) was excellent. Thus, it was excellent as an optical recording medium.

EXAMPLE 9

Instead of the dye used in Example 5, each of the compounds identified in Table 5 was prepared and coated on a substrate in the same manner as in Example 5 to obtain a substrate having a thin coating layer with the maximum asorption wavelength as identified in Table 5. To the thin coating layer thus obtained, writing was conducted by means of a semiconductor laser as a light source, whereby pits of uniform and clear shapes were obtained. The sensitivity and the C/N ratio were excellent. The initial characteristics (the dependency of sensitivity on the thickness of the recording layer, and the secondary distortion) were excellent. Yet, the storage stability was excellent. Thus, it was excellent as an optical recording medium.

In addition to the compounds used in the preceding Examples, specific examples of the metal-containing indoaniline compounds useful for the optical recording medium of the present invention include compounds identified in Table 6 and compounds of the formula IV wherein each of $X^1$, $X^2$ and $X^3$ is 2-$CH_3$, each of $Y^1$, $Y^2$ and $Y^3$ is a hydrogen atom, each of $R^7$, $R^8$, $R^9$, $R^{10}$, $R^{11}$ and $R^{12}$ is a hydrogen atom, and $R^1$, $R^2$, $R^3$, $R^4$, $R^5$, $R^6$, M and p are as identified in Table 7.

TABLE 5
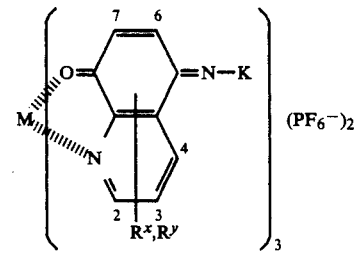
| Na | M | R$^x$ | R$^y$ | K | Maximum absorption wavelength of the thin coating layer (nm) |
|---|---|---|---|---|---|
| 9-1 | Ni | H | H | 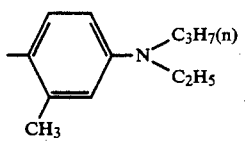 | 808 |
| 9-2 | " | " | " | 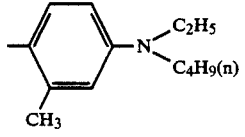 | 809 |
| 9-3 | Ni | H | H | 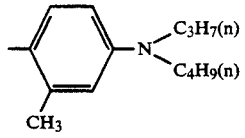 | 808 |
| 9-4 | " | " | " | 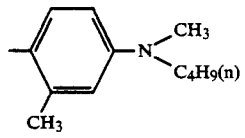 | 811 |
| 9-5 | " | " | " | 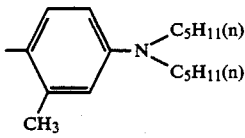 | 812 |
| 9-6 | " | " | " | 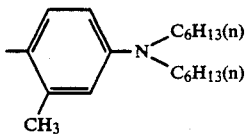 | 814 |
| 9-7 | Ni | 2-CH$_3$ | H | 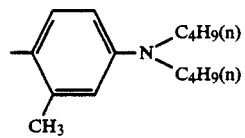 | 815 |
| 9-8 | " | " | " | 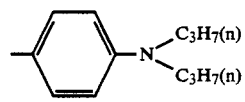 | 783 |

TABLE 5-continued $$\left\{ \begin{array}{c} \text{complex structure with positions 2,3,4,6,7, M, N, O, } R^x, R^y, \text{N-K} \end{array} \right\}_3 (PF_6^-)_2$$

| Na | M | $R^x$ | $R^y$ | K | Maximum absorption wavelength of the thin coating layer (nm) |
|---|---|---|---|---|---|
| 9-9 | " | 6- or 7-Cl | " | 3-CH₃, 4-methyl phenyl-N(C₂H₅)₂ | 835 |
| 9-10 | " | C₂H₅ | " | 3-CH₃, 4-methyl phenyl-N(C₂H₅)₂ | 808 |
| 9-11 | Ni | H | H | 3-C₂H₅, 4-methyl phenyl-N(C₂H₅)₂ | 808 |
| 9-12 | " | " | " | 3-C₃H₇(n), 4-methyl phenyl-N(C₂H₅)₂ | 809 |
| 9-13 | " | 6-CH₃ | " | 3-CH₃, 4-methyl phenyl-N(C₄H₉(n))₂ | 812 |
| 9-14 | " | H | " | 3,5-(CH₃)₂, 4-methyl phenyl-N(C₄H₉(n))₂ | 820 |
| 9-15 | Ni | H | H | 3-C₄H₉(n), 4-methyl phenyl-N(C₄H₉(n))₂ | 813 |
| 9-16 | Cu | " | " | 3-CH₃, 4-methyl phenyl-N(C₂H₅)₂ | 810 |

TABLE 5-continued
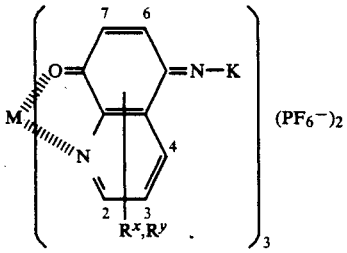
| Na | M | R$^x$ | R$^y$ | K | Maximum absorption wavelength of the thin coating layer (nm) |
|---|---|---|---|---|---|
| 9-17 | Co | " | " | 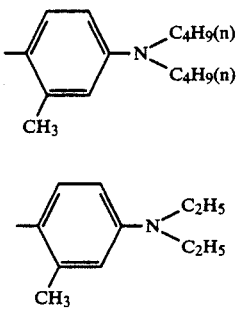 | 809 |
| 9-18 | Ni | 6- or 7-Cl | 2-CH$_3$ | 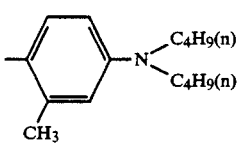 | 841 |
| 9-19 | Cu | H | H | 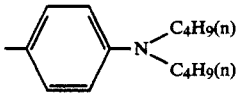 | 805 |
| 9-20 | " | " | " | 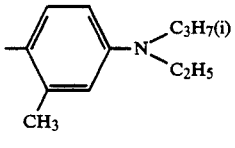 | 785 |
| 9-21 | Zn | " | " | 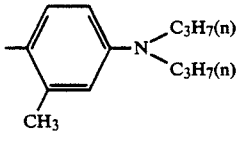 | 804 |
| 9-22 | " | " | " | 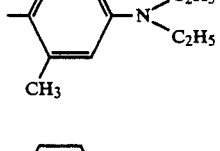 | 803 |
| 9-23 | Co | H | H | 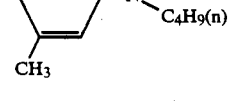 | 789 |
| 9-24 | " | " | " | (structure: N(C$_4$H$_9$(n))$_2$ with CH$_3$ on tolyl ring) | 791 |

TABLE 5-continued
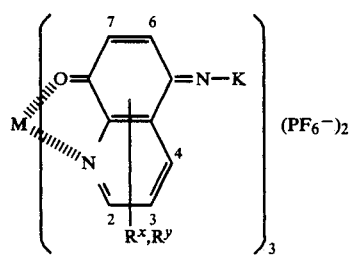
| Na | M | $R^x$ | $R^y$ | K | Maximum absorption wavelength of the thin coating layer (nm) |
|---|---|---|---|---|---|
| 9-25 | Cu | 6- or 6-Cl | 2-CH$_3$ | 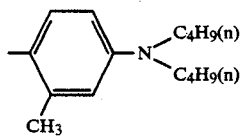 | 837 |
| 9-26 | Co | H | " | 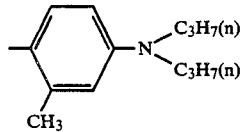 | 798 |
| 9-27 | Ni | H | H | 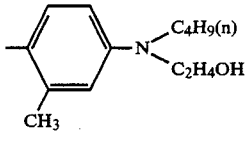 | 792 |
| 9-28 | " | " | " | 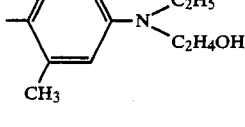 | 792 |
| 9-29 | " | " | " | 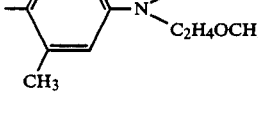 | 796 |
| 9-30 | " | " | " | 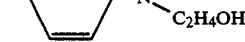 | 777 |
| 9-31 | Ni | H | H | 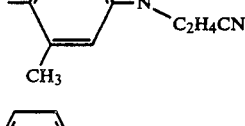 | 762 |
| 9-32 | " | " | " | 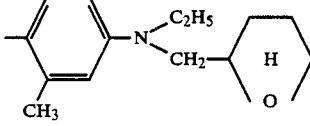 | 796 |

TABLE 5-continued $$\left\{ \begin{array}{c} \text{structure with } M, O, N-K, R^x, R^y \end{array} \right\}_3 (PF_6^-)_2$$

| Na | M | $R^x$ | $R^y$ | K | Maximum absorption wavelength of the thin coating layer (nm) |
|---|---|---|---|---|---|
| 9-33 | " | " | " | 4-methyl-3-methyl-phenyl-N(C$_2$H$_5$)(C$_2$H$_4$OC$_2$H$_4$OCH$_3$) | 796 |
| 9-34 | " | " | " | 4-methyl-3-methyl-phenyl-N(C$_2$H$_5$)(C$_2$H$_4$-phenyl) | 807 |
| 9-35 | Ni | H | H | 4-methyl-3-methyl-phenyl-N(C$_2$H$_5$)(C$_2$H$_4$O-phenyl) | 805 |
| 9-36 | " | " | " | 4-methyl-3-methyl-phenyl-N(C$_2$H$_5$)(C$_2$H$_4$OCH$_2$CH=CH$_2$) | 799 |
| 9-37 | " | " | " | 4-methyl-3-methyl-phenyl-N(C$_2$H$_5$)(C$_2$H$_4$NHSO$_3$CH$_3$) | 791 |
| 9-38 | " | " | " | 4-methyl-3-methyl-phenyl-N(C$_2$H$_5$)(C$_2$H$_4$OC$_2$H$_4$OC$_2$H$_4$OC$_2$H$_5$) | 796 |
| 9-39 | Ni | H | " | 4-methyl-3-methyl-phenyl-N(C$_2$H$_4$OCH$_3$)(C$_2$H$_4$OCH$_3$) | 789 |
| 9-40 | " | " | " | 4-methyl-3-methyl-phenyl-N(C$_2$H$_4$OH)(C$_2$H$_4$OH) | 778 |
| 9-41 | " | " | " | 4-methyl-3-methyl-phenyl-N(C$_2$H$_5$)(C$_2$H$_4$OCCH$_3$, C=O) | 788 |

TABLE 5-continued $$\left[M\left(\begin{array}{c}\text{structure with positions 2,3,4,6,7, O, N, =N-K, R}^x\text{,R}^y\end{array}\right)_3\right](PF_6^-)_2$$

| Na | M | R$^x$ | R$^y$ | K | Maximum absorption wavelength of the thin coating layer (nm) |
|---|---|---|---|---|---|
| 9-42 | " | " | " | 3-methyl-4-methyl-phenyl-N(C$_2$H$_4$OCH$_3$)(C$_2$H$_4$OCCH$_3$(=O)) | 774 |
| 9-43 | Ni | H | H | 3-methyl-4-methyl-phenyl-N(C$_2$H$_4$OC$_2$H$_4$OC$_2$H$_5$)$_2$ | 788 |
| 9-44 | " | " | " | 3-methyl-4-methyl-phenyl-N(C$_2$H$_4$OCCH$_3$(=O))$_2$ | 776 |
| 9-45 | " | " | " | 3-methyl-4-methyl-phenyl-N(C$_2$H$_4$OCH$_3$)(C$_2$H$_4$OC$_2$H$_4$OCH$_3$) | 786 |
| 9-46 | " | " | " | 3-methyl-4-methyl-phenyl-N(C$_2$H$_4$OCH$_2$CH=CH$_2$)$_2$ | 789 |
| 9-51 | Ni | H | H | 4-methyl-3-(NHCOOC$_2$H$_5$)-phenyl-N(C$_2$H$_5$)$_2$ | 803 |
| 9-52 | " | " | " | 4-methyl-3-(NHCO-phenyl)-phenyl-N(C$_2$H$_5$)$_2$ | 800 |
| 9-53 | " | " | " | 4-methyl-3-(NHSO$_2$C$_2$H$_5$)-phenyl-N(C$_2$H$_5$)$_2$ | 800 |

TABLE 5-continued $$\left\{ \begin{array}{c} \text{structure with } M, O, N, K, R^x, R^y \text{ substituents at positions 2,3,4,6,7} \end{array} \right\}_3 (PF_6^-)_2$$

| Na | M | $R^x$ | $R^y$ | K | Maximum absorption wavelength of the thin coating layer (nm) |
|---|---|---|---|---|---|
| 9-54 | " | " | " | 2,5-dimethyl-4-(N,N-diethylamino)-anisole (OCH₃, N(C₂H₅)₂, CH₃) | 816 |
| 9-55 | Ni | H | H | 2-Cl-5-NHCOCH₃-4-(N,N-diethylamino)toluene | 807 |
| 9-56 | " | " | " | 2-Cl-5-NHCOCH₃-4-(N-butylamino)toluene (C₄H₉, H) | 733 |
| 9-57 | " | " | " | 2-OCH₃-5-NHCOCH₃-4-(N,N-diethylamino)toluene | 830 |
| 9-58 | " | " | " | 2,5-di-OCH₃-4-(N,N-diethylamino)toluene | 809 |
| 9-59 | Ni | H | H | 3-NHCOCH₃-4-(N,N-di-n-pentylamino)toluene (C₅H₁₁(n))₂ | 818 |
| 9-60 | " | " | " | 3-NHCOCH₃-4-(N,N-di-n-propylamino)toluene (C₃H₇(n))₂ | 818 |
| 9-61 | " | " | " | 3-NHCOOCH₃-4-(N,N-diethylamino)toluene | 802 |

TABLE 5-continued
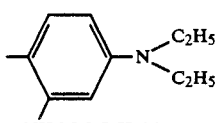
| Na | M | $R^x$ | $R^y$ | K | Maximum absorption wavelength of the thin coating layer (nm) |
|---|---|---|---|---|---|
| 9-62 | " | " | " | (aryl with N(C2H5)2 and NHCOOC3H7(n), CH3) | 801 |
| 9-63 | Ni | H | H | (aryl with morpholino, CH3) | 790 |
| 9-64 | " | " | " | (aryl with piperazinyl-NH, CH3) | 790 |
| 9-65 | " | 4-CH3 | 6-CH3 | (aryl with N(C4H9(n))2) | 813 |
| 9-66 | " | " | " | (aryl with N(C2H5)2 and C2H5) | 810 |
TABLE 6
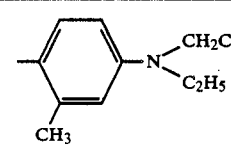
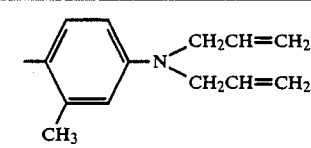
| M | $R^x$ | $R^y$ | K | M | $R^x$ | $R^y$ | K |
|---|---|---|---|---|---|---|---|
| Ni | H | H | (aryl with N(CH2CH=CH2)(C2H5), CH3) | " | " | " | (aryl with N(CH2CH=CH2)2, CH3) |

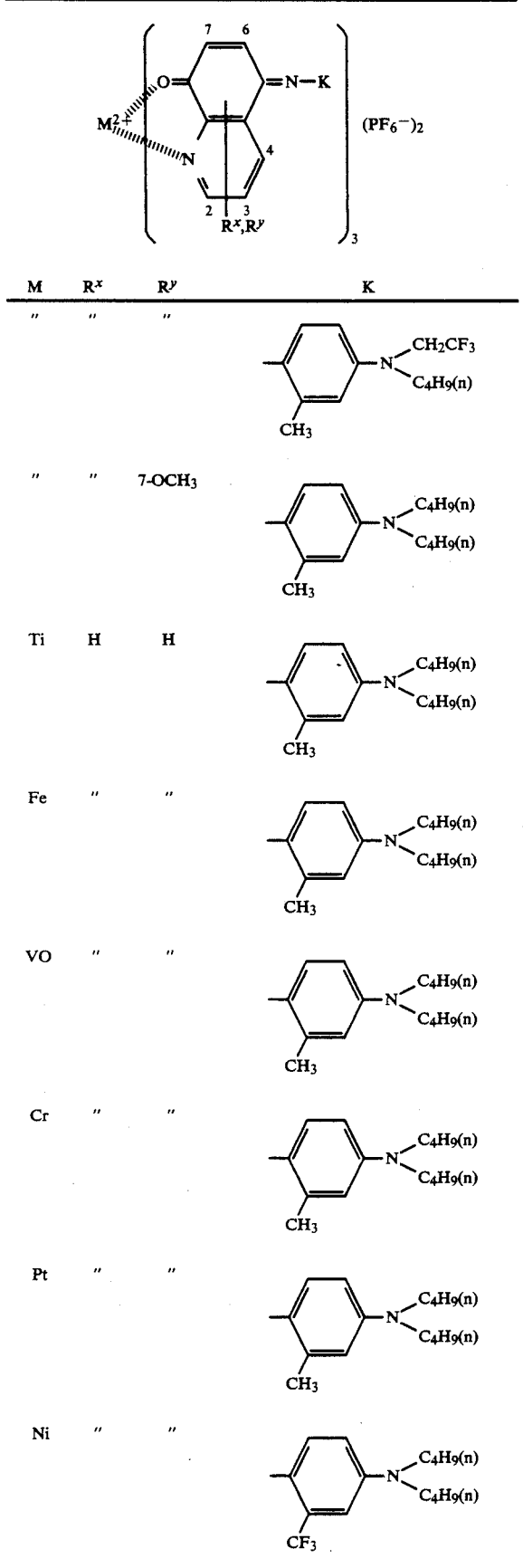
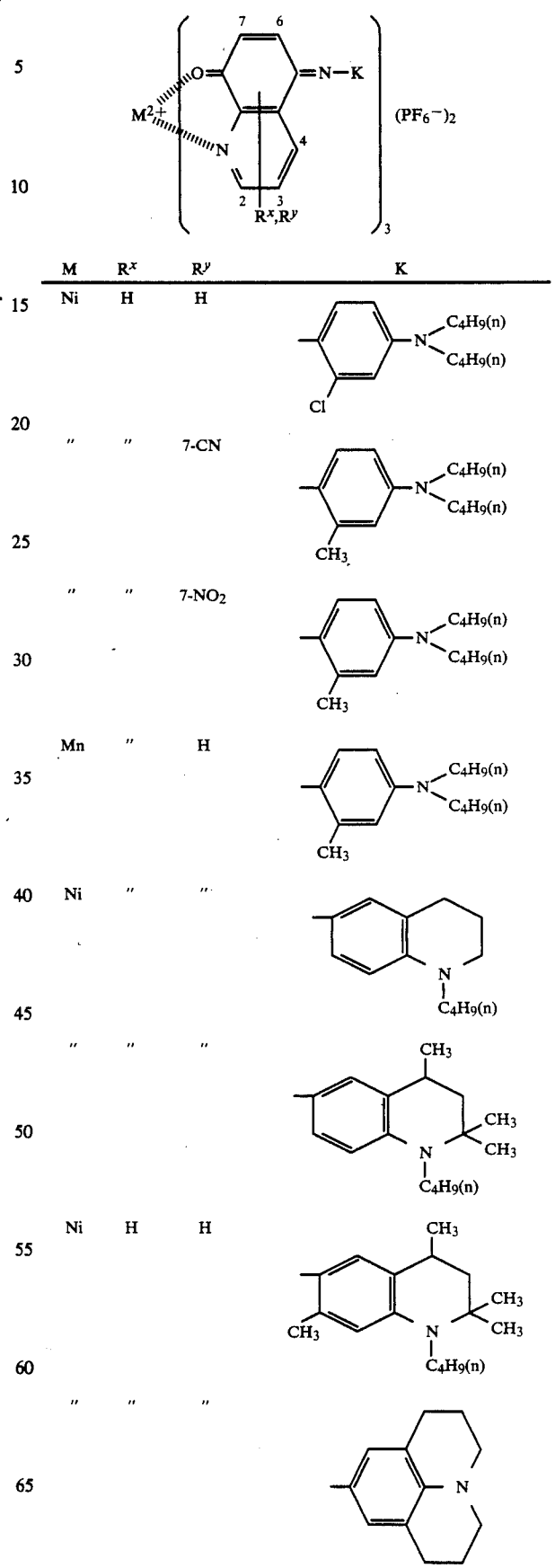

TABLE 6-continued

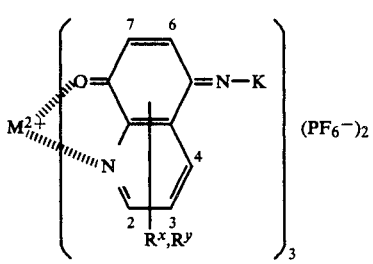

| M | R^x | R^y | K |
|---|---|---|---|
| " | " | " | 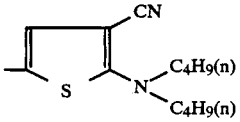 |
| " | " | " | 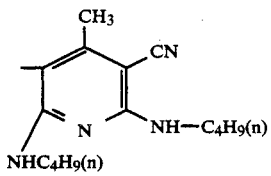 |
| " | " | " | 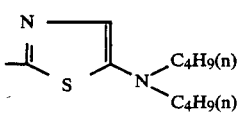 |
| ". | " | " | 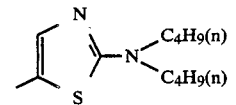 |

We claim:

1. A metal-containing indoaniline compound having the formula:

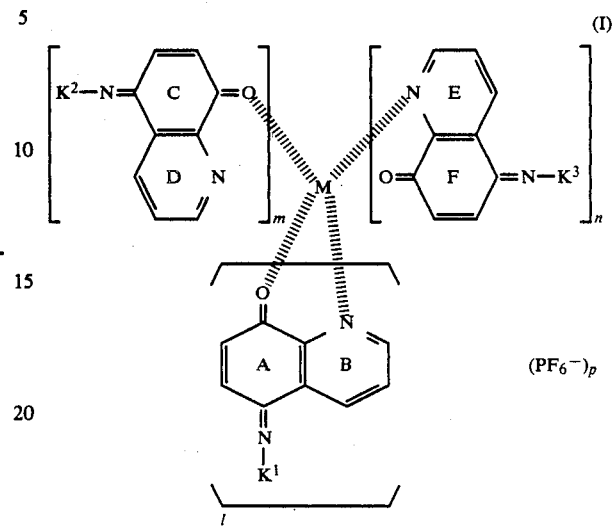

wherein M is a metal atom of Group VIII, Ib, IIb, IIIb, IVa, Va, VIa or VIIa of the Periodic Table or its halide or oxide, rings A, B, C, D, E and F may have substituents, each of $K^1$, $K^2$ and $K^3$ is a residue of a substituted or unsubstituted aromatic amine, each of 1, m and n is 0 or 1, provided $1+m+n=2$ or 3, and p is 2, 3 or 4.

2. The metal-containing indoaniline compound according to claim 1, which has the formula:

TABLE 7

| M | R^1 | R^2 | R^3 | R^4 | R^5 | R^6 | p |
|---|---|---|---|---|---|---|---|
| Ni | C_2H_5 | C_2H_5 | C_3H_7(n) | C_3H_7(n) | C_4H_9(n) | C_3H_7(n) | 2 |
| " | " | " | " | " | C_2H_5 | C_2H_4OC_2H_5 | " |
| " | " | " | " | " | C_4H_9(n) | C_2H_5 | " |
| Zn | " | " | " | " | C_5H_11(n) | C_5H_11(n) | " |
| Co | " | " | " | " | CH_2CH=CH_2 | CH_2CH=CH_2 | " |
| " | " | " | C_2H_5 | C_2H_5 | C_4H_9(n) | C_2H_4OCH_2CH=CH_2 | 3 |
| Co | C_2H_5 | C_2H_5 | C_2H_5 | C_2H_4OC_2H_5 | C_2H_4OC_2H_5 | C_2H_4OC_2H_5 | 3 |
| Al | " | " | " | " | C_4H_9(n) | " | " |
| Fe | " | " | " | " | " | C_2H_4OCH_3 | 3 |
| " | " | " | " | C_2H_5 | C_6H_13(n) | C_6H_13(n) | " |
| Al | " | " | " | " | C_4H_9(n) | C_2H_4OH | " |
| Ni | " | " | " | " | C_2H_5 | 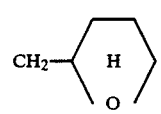 | 2 |

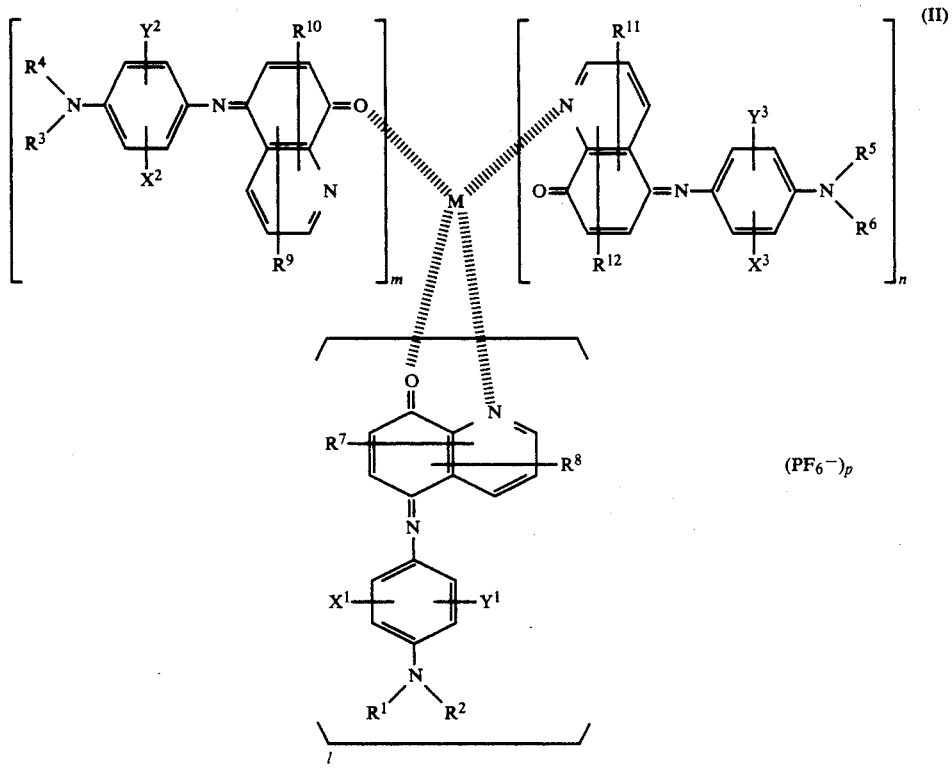

wherein M is a metal atom of Group VIII, Ib, IIb, IIIb, IVa, Va, VIa or VIIa of the Periodic Table, each of $R^7$, $R^8$, $R^9$, $R^{10}$, $R^{11}$, $R^{12}$, $X^1$, $X^2$, $X^3$, $Y^1$, $Y^2$ and $Y^3$ is a hydrogen atom, a halogen atom, an alkyl group, an alkoxy group, an acylamino group, an alkoxycarbonylamino group or an alkylsulfonylamino group, each of $R^1$, $R^2$, $R^3$, $R^4$, $R^5$ and $R^6$ is a hydrogen atom, a $C_{1-20}$ alkyl group, an aryl group, an alkenyl group or a cycloalkyl group, which may be substituted, each of l, m and n is 0 or 1, provided $1+m+n=2$ or 3, and p is 2, 3 or 4.

3. The metal-containing indoaniline compound according to claim 1, which has the formula:

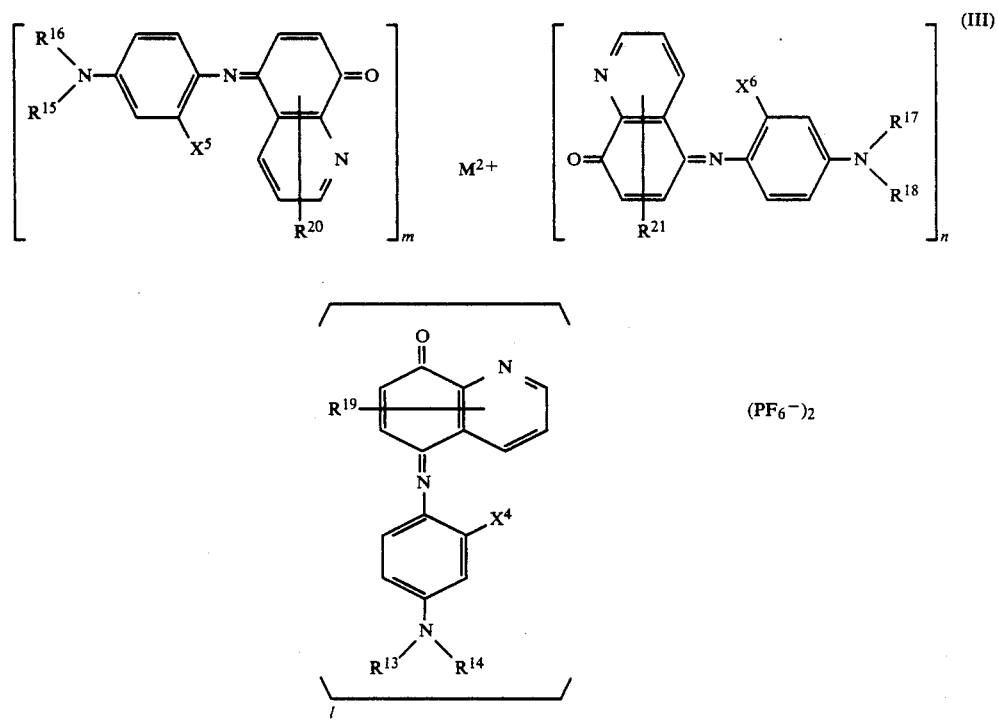

wherein M is a metal atom of Ni, Cu, Co, Zn or Fe, each of $X^4$, $X^5$ and $X^6$ is a hydrogen atom or a $C_{1-4}$ alkyl group, each of $R^{13}$, $R^{14}$, $R^{15}$, $R^{16}$, $R^{17}$ and $R^{18}$ is a $C_{1-8}$ alkyl group, an alkoxyalkyl group, an alkoxyalkoxyalkyl group, an alkoxyalkoxyalkoxyalkyl group, an allyloxyalkyl group, an arylalkyl group, an aryloxyalkyl group, a cyanoalkyl group, a hydroxyalkyl group, a tetrahydrofurylalkyl group, an alkylsulfonylaminoalkyl group, an acyloxyalkyl group or an alkenyl group, each of $R^{19}$, $R^{20}$ and $R^{21}$ is a hydrogen atom, a $C_{1-4}$ alkyl group or a halogen atom, and each of l, m and n is 0 or 1, provided $1+m+n=2$ or 3.

4. The metal-containing indoaniline compound according to claim 3, wherein in the formula III, each of $X^4$, $X^5$ and $X^6$ is a $C_{1-4}$ alkyl group, each of $R^{13}$, $R^{14}$, $R^{15}$, $R^{16}$, $R^{17}$ and $R^{18}$ is a $C_{1-6}$ alkyl group, and each of $R^{19}$, $R^{20}$ and $R^{21}$ is a hydrogen atom or a $C_{1-4}$ alkyl group.

5. An optical recording medium comprising a substrate and a recording layer containing a dye formed on the substrate wherein the recording is effected by irradiation of a laser beam to impart a thermal deformation to the recording layer and the reproduction is done by reading a difference in the reflectance between the deformed portion and the undeformed portion of the recording layer, said dye being a metal-containing indoaniline compound having the formula:

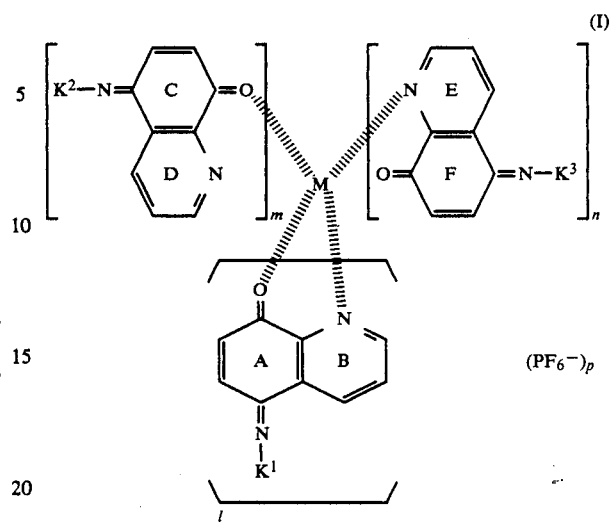

wherein M is a metal atom of Group VIII, Ib, IIb, IIIb, IVa, Va, VIa or VIIa of the Periodic Table or its halide or oxide, rings A, B, C, D, E and F may have substituents, each of $K^1$, $K^2$ and $K^3$ is a residue of a substituted or unsubstituted aromatic amine, each of l, m and n is 0 or 1, provided $1+m+n=2$ or 3, and p is 2, 3 or 4.

6. The optical recording medium according to claim 5, wherein the metal-containing indoaniline compound has the formula:

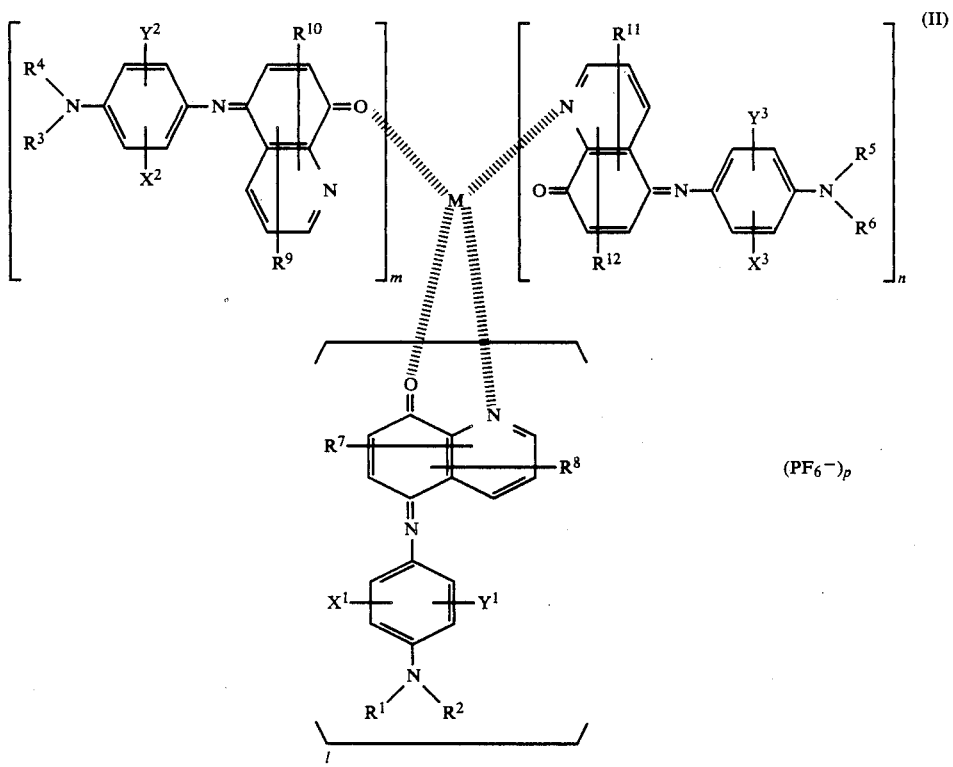

wherein M is a metal atom of Group VIII, Ib, IIb, IIIb, IVa, Va, VIa or VIIa of the Periodic Table, each of $R^7$, $R^8$, $R^9$, $R^{10}$, $R^{11}$, $R^{12}$, $X^1$, $X^2$, $X^3$, $Y^1$, $Y^2$ and $Y^3$ is a hydrogen atom, a halogen atom, an alkyl group, an alkoxy group, an acylamino group, an alkoxycarbonylamino group or an alkylsulfonylamino group, each of $R^1$, $R^2$, $R^3$, $R^4$, $R^5$ and $R^6$ is a hydrogen atom, a $C_{1-20}$ alkyl group, an aryl group, an alkenyl group or a cycloalkyl group, which may be substituted, each of l, m and n is 0 or 1, provided $1+m+n=2$ or 3, and p is 2, 3 or 4.

7. The optical recording medium according to claim 5, wherein the metal-containing indoaniline compound has the formula:

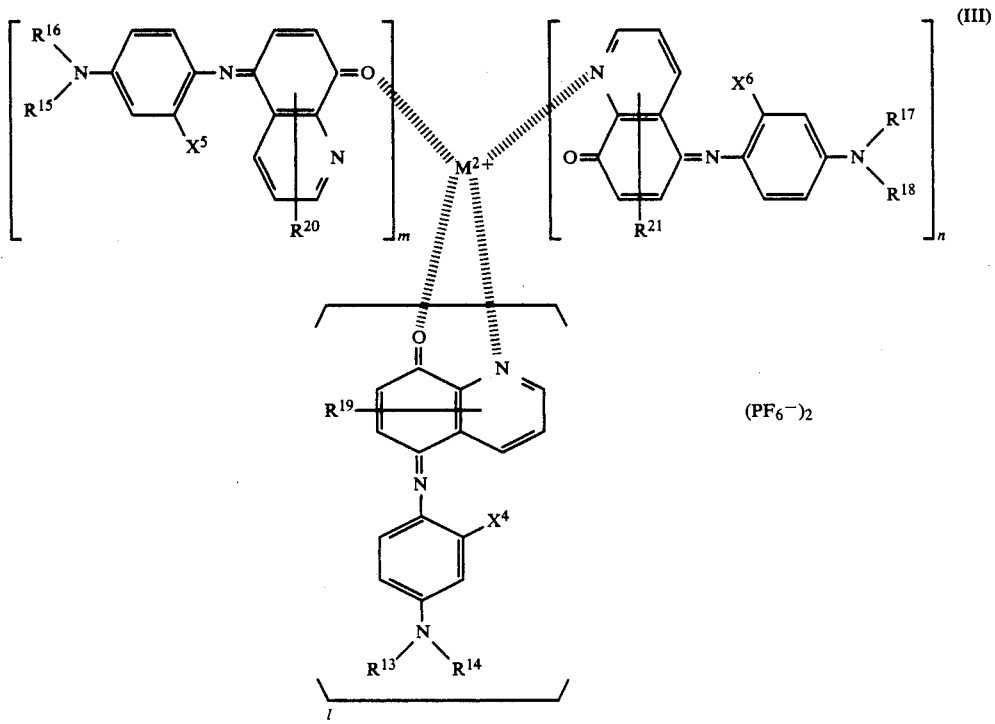

wherein M is a metal atom of Ni, Cu, Co, Zn or Fe, each of $X^4$, $X^5$ and $X^6$ is a hydrogen atom or a $C_{1-4}$ alkyl group, each of $R^{13}$, $R^{14}$, $R^{15}$, $R^{16}$, $R^{17}$ and $R^{18}$ is a $C_{1-8}$ alkyl group, an alkoxyalkyl group, an alkoxyalkoxyalkyl group, an alkoxyalkoxyalkoxyalkyl group, an al- lyloxyalkyl group, an arylalkyl group, an aryloxyalkyl group, a cyanoalkyl group, a hydroxyalkyl group, a tetrahydrofurylalkyl group, an alkylsulfonylaminoalkyl group, an acyloxyalkyl group or an alkenyl group, each of $R^{19}$, $R^{20}$ and $R^{21}$ is a hydrogen atom, a $C_{1-4}$ alkyl group or a halogen atom, and each of l, m and n is 0 or 1, provided $1+m+n=2$ or 3.

8. The optical recording medium according to claim 7, wherein in the formula III, each $X^4$, $X^5$ and $X^6$ is a $C_{1-4}$ alkyl group, each of $R^{13}$, $R^{14}$, $R^{15}$, $R^{16}$, $R^{17}$ and $R^{18}$ is a $C_{1-6}$ alkykl group, and each of $R^{19}$, $R^{20}$ and $R^{21}$ is a hydrogen atom or a $C_{1-4}$ alkyl group.

* * * * *